US008936909B2

(12) United States Patent
Lubenow et al.

(10) Patent No.: US 8,936,909 B2
(45) Date of Patent: Jan. 20, 2015

(54) METHOD FOR DETERMINING THE ORIGIN OF A SAMPLE

(75) Inventors: Helge Lubenow, Langenfeld (DE); Jack Ballantyne, Chuluota, FL (US); Erin K. Hanson, Oviedo, FL (US)

(73) Assignees: Qiagen GmbH, Hilden (DE); University of Central Florida Research Foundation Inc., Orlando, FL (US)

( * ) Notice: Subject to any disclaimer, the term of this patent is extended or adjusted under 35 U.S.C. 154(b) by 448 days.

(21) Appl. No.: 13/054,721

(22) PCT Filed: Jul. 20, 2009

(86) PCT No.: PCT/EP2009/005254
§ 371 (c)(1),
(2), (4) Date: Jan. 4, 2012

(87) PCT Pub. No.: WO2010/006814
PCT Pub. Date: Jan. 21, 2010

(65) Prior Publication Data
US 2012/0094850 A1 Apr. 19, 2012

Related U.S. Application Data

(60) Provisional application No. 61/082,056, filed on Jul. 18, 2008.

(51) Int. Cl.
*C12Q 1/68* (2006.01)
(52) U.S. Cl.
CPC .................................. *C12Q 1/6881* (2013.01)
USPC ........................................... 435/6.1; 435/6.12

(58) Field of Classification Search
None
See application file for complete search history.

(56) References Cited

U.S. PATENT DOCUMENTS

| 7,270,983 | B1 | 9/2007 | Ballantyne |
| 8,039,234 | B1 * | 10/2011 | Fang et al. .................. 435/91.1 |
| 2005/0123952 | A1 | 6/2005 | Griffrey |

FOREIGN PATENT DOCUMENTS

| WO | WO 2007/073737 A | 7/2007 |
| WO | WO 2007073737 A1 * | 7/2007 |
| WO | WO 2008/020008 | 2/2008 |
| WO | WO 2008/029295 | 3/2008 |

OTHER PUBLICATIONS

Hanson et al., "Identification of forensically relevant body fluids using a panel of differentially expressed microRNAs," Anal. Biochem. 2009, 387:303-314.*

Zubakov et al., "MicroRNA markers for forensic body fluid identification obtained from microarray screening and quantitative RT-PCR confirmation," Int. J. Legal Med. 2010, 124:217-226.*

(Continued)

*Primary Examiner* — Samuel Woolwine
*Assistant Examiner* — Kaijiang Zhang
(74) *Attorney, Agent, or Firm* — Fanelli Haag & Kilger PLLC

(57) ABSTRACT

A method for determining the nature of a sample is provided, wherein the presence or absence of at least one marker small non-coding RNA in the sample is detected. Suitable marker small non-coding RNAs for different samples such as blood, saliva, semen and vaginal secretions are provided. Also provided are suitable kits and methods for identifying marker small-non coding RNAs.

7 Claims, 15 Drawing Sheets

(56) References Cited

OTHER PUBLICATIONS

Wang et al., "A model for data analysis of microRNA expression in forensic body fluid identification," Forensic Sci. Int. Genet. 2012, 6:419-423.*

Chajut, A. et al., "MicroRNA profiles in body fluids as a novel class of biomarkers," Proceedings of the Annual Meeting of the American Association for Cancer Research, New York, NY, US vol. 49, Apr. 16, 2008, p. 1231.

Labourier, E. and Goldrick, M., "MiRNA Expression in White Blood Cells," Applied Biosystems Technotes [Online] vol. 11 No. 3, May 2004, pp. 2-3.

Beuvink, Iwan et al., "A novel microarray approach reveals new tissue-specific signatures of known and predicted mammalian microRNAs," Nucleic Acids Research vol. 35 No. 7, Apr. 2007, p. 3.

Lagos-Quintana, M et al., "Identification of novel genes coding for small expressed RNAs," Science, American Association for the Advancement of Science, US, Washington, DC vol. 294 No. 5543, Oct. 26, 2001, pp. 853-858.

Sewer, Alain et al., "Identification of clustered microRNAs using an ab initio prediction method," BMC Bioinformatics 2005, vol. 6, p. 267.

Weber, Michel J, "New human and mouse microRNA genes found by homology search," FEBS Journal vol. 272 No. 1, Jan. 2005, pp. 59-73.

Suh, Mi-ra et al., "Human embryonic stem cells express a unique set of microRNAs," Developmental Biology, Academic Press, New York, NY, US vol. 270 No. 2, May 6, 2004, pp. 488-498.

Lagos-Quintana, Mariana et al., "New microRNAs from mouse and human, RNA," Cold Spring Harbor Laboratory Press Woodbury, NY, US vol. 9 No. 2, Feb. 1, 2003, pp. 175-179.

Jobling et al., "Encoded Evidence: DNA in Forensic Analysis," Nature Reviews in Genetics, vol. 5, p. 739; 2004.

Mattick et al., "Non-coding RNA," Human Molecular Genetics 2006, vol. 15, Review Issue 1 R17-R29.

Cummins et al., "Implications of micro-RNA profiling for cancer diagnosis," Oncogene (2006) 25, pp. 6220-6227.

Berezikov et al., "Approaches to microRNA discovery," Nature Genetics Supplement, vol. 38, Jun. 2006, pp. S2-S7.

Kloosterman et al., "The Diverse Functions of MicroRNAs in Animal Development and Disease," Developmental Cell 11, Oct. 2006 pp. 441-450.

Chomczynski et al., "The single-step method of RNA isolation by acid guanidinium thiocyanate-phenol-chloroform extraction: twenty-something years on," Analytical Biochemistry Apr. 1987; 162: pp. 156-159.

Nussbaumer et al., "Messenger RNA profiling: A novel method for body fluid identification by Real-Time PCR," Forensic Science International, 157 (2006) pp. 181-186.

Juusola et al., "Multiplex mRNA profiling for the identification of body fluids," Forensic Science International, 152 (2005) pp. 1-12.

* cited by examiner

Table 1: Small non-coding RNAs suitable as blood markers

| miRNA | Human miRNAs |
|---|---|
| let7a | hsa-let-7a-UGAGGUAGUAGGUUGUAUAGUU - SEQ ID NO: 1 |
| let7b | hsa-let-7b-UGAGGUAGUAGGUUGUGUGGUU - SEQ ID NO 2 |
| let7c | hsa-let-7c-UGAGGUAGUAGGUUGUAUGGUU - SEQ ID NO: 3 |
| let7d | hsa-let-7d-AGAGGUAGUAGGUUGCAUAGUU - SEQ ID NO: 4 |
| let7e | hsa-let-7e-UGAGGUAGGAGGUUGUAUAGUU - SEQ ID NO: 5 |
| let7f | hsa-let-7f-UGAGGUAGUAGAUUGUAUAGUU - SEQ ID NO: 6 |
| let7g | hsa-let-7g-UGAGGUAGUAGUUUGUACAGUU - SEQ ID NO: 7 |
| let7i | hsa-let-7i-UGAGGUAGUAGUUUGUGCUGUU - SEQ ID NO: 8 |
| miR7 | hsa-miR-7-UGGAAGACUAGUGAUUUUGUUGU - SEQ ID NO: 9 |
| miR15a | hsa-miR-15a-UAGCAGCACAUAAUGGUUUGUG - SEQ ID NO: 10 |
| miR15b | hsa-miR-15b-UAGCAGCACAUCAUGGUUUACA - SEQ ID NO: 11 |
| miR16 | hsa-miR-16-UAGCAGCACGUAAAUAUUGGCG - SEQ ID NO: 12 |
| miR17 | hsa-miR-17-CAAAGUGCUUACAGUGCAGGUAG - SEQ ID NO: 13 |
| miR18a/b | hsa-miR-18a-UAAGGUGCAUCUAGUGCAGAUAG - SEQ ID NO: 14 |
| | hsa-miR-18b-UAAGGUGCAUCUAGUGCAGUUAG - SEQ ID NO: 15 |
| miR18a* | hsa-miR-18a*-ACUGCCCUAAGUGCUCCUUCUGG - SEQ ID NO: 16 |
| miR19a | hsa-miR-19a-UGUGCAAAUCUAUGCAAAACUGA - SEQ ID NO: 17 |
| miR20a | hsa-miR-20a-UAAAGUGCUUAUAGUGCAGGUAG - SEQ ID NO: 18 |
| miR25 | hsa-miR-25-CAUUGCACUUGUCUCGGUCUGA - SEQ ID NO: 19 |
| miR26b | hsa-miR-26b-UUCAAGUAAUUCAGGAUAGGU - SEQ ID NO: 20 |
| miR30b | hsa-miR-30b-UGUAAACAUCCUACACUCAGCU - SEQ ID NO: 21 |
| miR30a/e-5p | hsa-miR-30a-UGUAAACAUCCUCGACUGGAAG - SEQ ID NO: 22 |
| | hsa-miR-30e- UGUAAACAUCCUUGACUGGAAG – preferred - SEQ ID NO: 23 |
| miR93 | hsa-miR-93-CAAAGUGCUGUUCGUGCAGGUAG - SEQ ID NO: 24 |
| miR96 | hsa-miR-96-UUUGGCACUAGCACAUUUUUGCU - SEQ ID NO: 25 |
| miR103 | hsa-miR-103-AGCAGCAUUGUACAGGGCUAUGA - SEQ ID NO: 26 |
| | // hsa-miR-107-AGCAGCAUUGUACAGGGCUAUCA - SEQ ID NO: 29 |
| miR106a | hsa-miR-106a-AAAAGUGCUUACAGUGCAGGUAG - SEQ ID NO: 27 |
| | // hsa-miR-17-CAAAGUGCUUACAGUGCAGGUAG - SEQ ID NO: 13 |
| miR106b | hsa-miR-106b-UAAAGUGCUGACAGUGCAGAU - SEQ ID NO: 28 |
| miR107 | hsa-miR-107-AGCAGCAUUGUACAGGGCUAUCA - SEQ ID NO: 29 |
| miR126 | hsa-miR-126-UCGUACCGUGAGUAAUAAUGCG - SEQ ID NO: 30 |
| miR126* | hsa-miR-126*-CAUUAUUACUUUUGGUACGCG - SEQ ID NO: 31 |
| miR128 | has-miR-128-UCACAGUGAACCGGUCUCUUU - SEQ ID NO: 32 |
| miR130a | hsa-miR-130a-CAGUGCAAUGUUAAAAGGGCAU - SEQ ID NO: 33 |
| miR148b | hsa-miR-148a-UCAGUGCACUACAGAACUUUGU - SEQ ID NO: 34 |
| | hsa-miR-148b-UCAGUGCAUCACAGAACUUUGU - SEQ ID NO: 35 |
| | hsa-miR-148a*-AAAGUUCUGAGACACUCCGACU - SEQ ID NO: 36 |
| | hsa-miR-148b*-AAGUUCUGUUAUACACUCAGGC - SEQ ID NO: 37 |
| miR150 | hsa-miR-150-UCUCCCAACCCUUGUACCAGUG - SEQ ID NO: 38 |
| miR151 | hsa-miR-151-5p-UCGAGGAGCUCACAGUCUAGU - SEQ ID NO: 39 |
| | hsa-miR-151-3p-CUAGACUGAAGCUCCUUGAGG – preferred - SEQ ID NO: 40 |
| miR181a | hsa-miR-181a-AACAUUCAACGCUGUCGGUGAGU - SEQ ID NO: 41 |
| miR181c | hsa-miR-181c-AACAUUCAACCUGUCGGUGAGU - SEQ ID NO: 42 |

FIG. 1

| | | |
|---|---|---|
| miR182 | hsa-miR-182-UUUGGCAAUGGUAGAACUCACACU - SEQ ID NO: 43 | |
| miR182* | hsa-miR-182*-UGGUUCUAGACUUGCCAACUA - SEQ ID NO: 44 | |
| miR183 | hsa-miR-183-UAUGGCACUGGUAGAAUUCACU - SEQ ID NO: 45 | |
| miR185 | hsa-miR-185-UGGAGAGAAAGGCAGUUCCUGA - SEQ ID NO: 46 | |
| miR190 | hsa-miR-190-UGAUAUGUUUGAUAUAUUAGGU - SEQ ID NO: 47 | |
| miR191 | hsa-miR-191-CAACGGAAUCCCAAAAGCAGCUG - SEQ ID NO: 48 | |
| miR194 | hsa-miR-194-UGUAACAGCAACUCCAUGUGGA - SEQ ID NO: 49 | |
| miR195 | hsa-miR-195-UAGCAGCACAGAAAUAUUGGC - SEQ ID NO: 50 | |
| miR210 | hsa-miR-210-CUGUGCGUGUGACAGCGGCUGA - SEQ ID NO: 51 | |
| miR215 | hsa-miR-215-AUGACCUAUGAAUUGACAGAC - SEQ ID NO: 52 | |
| miR301 | hsa-miR-301a-CAGUGCAAUAGUAUUGUCAAAGC – preferred - SEQ ID NO: 53 | |
| | hsa-miR-301b-CAGUGCAAUGAUAUUGUCAAAGC - SEQ ID NO: 54 | |
| miR324-3p | hsa-miR-324-3p-ACUGCCCCAGGUGCUGCUGG - SEQ ID NO: 55 | |
| miR331 | hsa-miR-331-3p-GCCCCUGGGCCUAUCCUAGAA - preferred - SEQ ID NO: 56 | |
| | hsa-miR-331-5p-CUAGGUAUGGUCCCAGGGAUCC - SEQ ID NO: 57 | |
| miR324-3p | hsa-miR-324-3p-ACUGCCCCAGGUGCUGCUGG - SEQ ID NO: 55 | |
| miR339 | hsa-miR-339-5p-UCCCUGUCCUCCAGGAGCUCACG – preferred - SEQ ID NO: 58 | |
| | hsa-miR-339-3p-UGAGCGCCUCGACGACAGAGCCG - SEQ ID NO: 59 | |
| miR340 | hsa-miR-340-UUAUAAAGCAAUGAGACUGAUU - SEQ ID NO: 60 | |
| miR363* | hsa-miR-363*-CGGGUGGAUCACGAUGCAAUUU - SEQ ID NO: 61 | |
| miR374 | hsa-miR-374-UUAUAAUACAACCUGAUAAGUG - SEQ ID NO: 62 | |
| miR425 | hsa-miR-425-AAUGACACGAUCACUCCCGUUGA - SEQ ID NO: 63 | |
| miR451 | hsa-miR-451-AAACCGUUACCAUUACUGAGUU - SEQ ID NO: 119 | |
| miR484 | hsa-miR-484-UCAGGCUCAGUCCCCUCCCGAU - SEQ ID NO: 120 | |
| miR486 | hsa-miR-486-5p-UCCUGUACUGAGCUGCCCCGAG – preferred - SEQ ID NO: 64 | |
| | hsa-miR-486-3p-CGGGGCAGCUCAGUACAGGAU - SEQ ID NO: 65 | |
| miR500 | hsa-miR-500-UAAUCCUUGCUACCUGGGUGAGA - SEQ ID NO: 66 | |
| miR545 | hsa-miR-545-UCAGCAAACAUUUAUUGUGUGC - SEQ ID NO: 67 | |
| miR548d | hsa-miR-548d-5p-AAAAGUAAUUGUGGUUUUUGCC - SEQ ID NO: 68 | |
| | hsa-miR-548d-3p-CAAAAACCACAGUUUCUUUUGC – preferred - SEQ ID NO: 69 | |
| miR556 | hsa-miR-556-3p-AUAUUACCAUUAGCUCAUCUUU - SEQ ID NO: 70 | |
| | hsa-miR-556-5p-GAUGAGCUCAUUGUAAUAUGAG – preferred - SEQ ID NO: 71 | |
| miR576 | hsa-miR-576-3p-AAGAUGUGGAAAAAUUGGAAUC - SEQ ID NO: 72 | |
| | hsa-miR-576-5p-AUUCUAAUUUCUCCACGUCUUU – preferred - SEQ ID NO: 73 | |
| miR579 | hsa-miR-579-UUCAUUUGGUAUAAACCGCGAUU - SEQ ID NO: 74 | |
| miR580 | hsa-miR-580-UUGAGAAUGAUGAAUCAUUAGG - SEQ ID NO: 75 | |
| miR581 | hsa-miR-581-UCUUGUGUUCUCUAGAUCAGU - SEQ ID NO: 76 | |
| miR590 | hsa-miR-590-5p-GAGCUUAUUCAUAAAAGUGCAG – preferred - SEQ ID NO: 77 | |
| | hsa-miR-590-3p-UAAUUUUAUGUAUAAGCUAGU - SEQ ID NO: 78 | |
| miR624 | hsa-miR-624-CACAAGGUAUUGGUAUUACCU - SEQ ID NO: 79 | |
| miR627 | hsa-miR-627-GUGAGUCUCUAAGAAAAGAGGA - SEQ ID NO: 80 | |
| miR651 | hsa-miR-651-UUUAGGAUAAGCUUGACUUUUG - SEQ ID NO: 81 | |
| miR652 | hsa-miR-652-AAUGGCGCCACUAGGGUUGUG - SEQ ID NO: 82 | |
| miR660 | hsa-miR-660-UACCCAUUGCAUAUCGGAGUUG - SEQ ID NO: 83 | |
| miR154* | hsa-miR-154*-AAUCAUACACGGUUGACCUAUU - SEQ ID NO: 84 | |
| miR607 | hsa-miR-607-GUUCAAAUCCAGAUCUAUAAC - SEQ ID NO: 85 | |

FIG. 1(continued)

Table 2: Small non-coding RNAs as marker for menstrual blood

| miRNA | Human miRNAs |
|---|---|
| miR23 a/b | hsa-miR-23a-AUCACAUUGCCAGGGAUUUCC - preferred - SEQ ID NO: 86 |
| | hsa-miR-23b-AUCACAUUGCCAGGGAUUACC - SEQ ID NO: 87 |
| miR27b | hsa-miR-27b-UUCACAGUGGCUAAGUUCUGC - SEQ ID NO: 88 |
| miR31 | hsa-miR-31-AGGCAAGAUGCUGGCAUAGCU - SEQ ID NO: 89 |
| miR33 | hsa-miR-33 -GUGCAUUGUAGUUGCAUUGCA - SEQ ID NO: 90 |
| miR33b | hsa-miR-33b-GUGCAUUGCUGUUGCAUUGC - SEQ ID NO: 91 |
| miR95 | hsa-miR-95-UUCAACGGGUAUUUAUUGAGCA - SEQ ID NO: 92 |
| miR106b | hsa-miR-106b-UAAAGUGCUGACAGUGCAGAU - SEQ ID NO: 28 |
| miR125a | hsa-miR-125a-3p-ACAGGUGAGGUUCUUGGGAGCC - SEQ ID NO: 93 |
| | hsa-miR-125a-5p-UCCCUGAGACCCUUUAACCUGUGA – preferred - SEQ ID NO:94 |
| miR125b | hsa-miR-125b-UCCCUGAGACCCUAACUUGUGA - SEQ ID NO: 95 |
| miR136 | hsa-miR-136-ACUCCAUUUGUUUUGAUGAUGGA - SEQ ID NO: 96 |
| miR141 | hsa-miR-141-UAACACUGUCUGGUAAAGAUGG - SEQ ID NO: 97 |
| miR143 | hsa-miR-143-UGAGAUGAAGCACUGUAGCUC - SEQ ID NO: 98 |
| miR154 | hsa-miR-154-UAGGUUAUCCGUGUUGCCUUCG - SEQ ID NO: 99 |
| miR181b | hsa-miR-181b-AACAUUCAUUGCUGUCGGUGGGU - SEQ ID NO: 100 |
| miR24* | hsa – miR24* - UGCCUACUGAGCUGAUAUCAGU - SEQ ID NO: 101 |
| miR193b | hsa-miR-193b-AACUGGCCCUCAAAGUCCCGCU - SEQ ID NO: 102 |
| miR199a | hsa-miR-199a-3p-ACAGUAGUCUGCACAUUGGUUA - SEQ ID NO: 103 |
| | hsa-miR-199a-5p-CCCAGUGUUCAGACUACCUGUUC – preferred - SEQ ID NO: 104 |
| miR199b | hsa-miR-199b-5p-CCCAGUGUUUAGACUAUCUGUUC – preferred - SEQ ID NO: 105 |
| | hsa-miR-199b-3p-ACAGUAGUCUGCACAUUGGUUA - SEQ ID NO: 103 |
| miR200b | hsa-miR-200b-UAAUACUGCCUGGUAAUGAUGA - SEQ ID NO: 106 |
| miR200c | hsa-miR-200c-UAAUACUGCCGGGUAAUGAUGGA - SEQ ID NO: 107 |
| miR203 | hsa-miR-203-GUGAAAUGUUUAGGACCACUAG - SEQ ID NO: 108 |
| miR218 | hsa-miR-218-UUGUGCUUGAUCUAACCAUGU - SEQ ID NO: 109 |
| miR223 | hsa-miR-223-UGUCAGUUUGUCAAAUACCCCA - SEQ ID NO: 110 |
| miR337 | hsa-miR-337-3p-CUCCUAUAUGAUGCCUUUCUUC – preferred - SEQ ID NO: 111 |
| | hsa-miR-337-5p-GAACGGCUUCAUACAGGAGUU - SEQ ID NO: 112 |
| miR377 | hsa-miR-377-AUCACACAAAGGCAACUUUUGU - SEQ ID NO: 113 |
| miR382 | hsa-miR-382-GAAGUUGUUCGUGGUGGAUUCG - SEQ ID NO: 114 |
| miR412 | hsa-miR-412-ACUUCACCUGGUCCACUAGCCGU - SEQ ID NO: 115 |
| miR423 | hsa-miR-423-3p-AGCUCGGUCUGAGGCCCCUCAGU – preferred - SEQ ID NO: 116 |
| | hsa-miR-423-5p-UGAGGGGCAGAGAGCGAGACUUU - SEQ ID NO: 117 |
| miR425-3p | hsa-miR-425-3p – UAGUGCAAUAUUGCUUAUAGGGU - SEQ ID NO: 118 |
| miR451 | hsa-miR-451-AAACCGUUACCAUUACUGAGUU - SEQ ID NO: 119 |
| miR484 | hsa-miR-484-UCAGGCUCAGUCCCCUCCCGAU - SEQ ID NO: 120 |
| miR384 | hsa-miR-384-AUUCCUAGAAAUUGUUCAUA - SEQ ID NO: 121 |
| miR382 | hsa-miR-382-GAAGUUGUUCGUGGUGGAUUCG - SEQ ID NO: 114 |
| miR429 | hsa-miR-429-UAAUACUGUCUGGUAAAACCGU - SEQ ID NO: 122 |
| miR431 | hsa-miR-431-UGUCUUGCAGGCCGUCAUGCA - SEQ ID NO: 123 |
| miR452 | hsa-miR-452-AACUGUUUGCAGAGGAAACUGA - SEQ ID NO: 124 |
| miR452* | hsa-miR-452*-CUCAUCUGCAAAGAAGUAAGUG - SEQ ID NO: 125 |
| miR494 | hsa-miR-494-UGAAACAUACACGGGAAACCUC - SEQ ID NO: 126 |

FIG. 2

| | |
|---|---|
| miR497 | hsa-miR-497-CAGCAGCACACUGUGGUUUGU - SEQ ID NO: 127 |
| miR517* | hsa-miR-517*-CCUCUAGAUGGAAGCACUGUCU - SEQ ID NO: 128 |
| miR611 | hsa-miR-611-GCGAGGACCCCUCGGGGUCUGAC - SEQ ID NO: 176 |
| miR633 | hsa-miR-633-CUAAUAGUAUCUACCACAAUAAA - SEQ ID NO: 129 |
| miR637 | hsa-miR-637-ACUGGGGGCUUUCGGGCUCUGCGU - SEQ ID NO: 130 |
| miR641 | hsa-miR-641-AAAGACAUAGGAUAGAGUCACCUC - SEQ ID NO: 131 |
| miR648 | hsa-miR-648-AAGUGUGCAGGGCACUGGU - SEQ ID NO: 132 |
| miR211 | hsa-miR-211-UUCCCUUUGUCAUCCUUCGCCU - SEQ ID NO: 133 |
| miR216 | hsa-miR-216a-UAAUCUCAGCUGGCAACUGUGA – preferred - SEQ ID NO: 192 |
| | hsa-miR-216b-AAAUCUCUGCAGGCAAAUGUGA - SEQ ID NO: 191 |
| miR369-5p | hsa-miR-369-5p-AGAUCGACCGUGUUAUAUUCGC - SEQ ID NO: 134 |
| miR376a/b | hsa-miR-376a-AUCAUAGAGGAAAAUCCACGU - SEQ ID NO: 135 |
| | hsa-miR-376b-AUCAUAGAGGAAAAUCCAUGUU - SEQ ID NO: 136 |
| miR379 | hsa-miR-379-UGGUAGACUAUGGAACGUAGG - SEQ ID NO: 137 |
| miR489 | hsa-miR-489-GUGACAUCACAUAUACGGCAGC - SEQ ID NO: 138 |
| miR507 | hsa-miR-507-UUUUGCACCUUUUGGAGUGAA - SEQ ID NO: 139 |

FIG. 2(continued)

Table 3: Small non-coding RNAs as marker for semen

| miRNA | Human miRNAs |
|---|---|
| miR10b | hsa-miR-10b-UACCCUGUAGAACCGAAUUGUG - SEQ ID NO: 140 |
| miR99a | hsa-miR-99a-AACCCGUAGAUCCGAUCUUGUG - SEQ ID NO: 141 |
| miR100 | hsa-miR-100-AACCCGUAGAUCCGAACUUGUG - SEQ ID NO: 142 |
| miR135a | hsa-miR-135a-UAUGGCUUUUUAUUCCUAUGUGA - SEQ ID NO: 143 |
| miR135b | hsa-miR-135b-UAUGGCUUUUCAUUCCUAUGUGA - SEQ ID NO: 144 |
| miR149 | hsa-miR-149-UCUGGCUCCGUGUCUUCACUCCC - SEQ ID NO: 145 |
| miR204 | hsa-miR-204-UUCCCUUUGUCAUCCUAUGCCU - SEQ ID NO: 146 |
| miR449 | hsa-miR-449a-UGGCAGUGUAUUGUUAGCUGGU – preferred - SEQ ID NO: 147 |
| | hsa-miR-449b-AGGCAGUGUAUUGUUAGCUGGC - SEQ ID NO: 148 |
| miR508 | hsa-miR-508-3p-UGAUUGUAGCCUUUUGGAGUAGA – preferred - SEQ ID NO: 149 |
| | hsa-miR-508-5p-UACUCCAGAGGGCGUCACUCAUG - SEQ ID NO: 150 |
| miR513 | hsa-miR-513-UUCACAGGGAGGUGUCAU - SEQ ID NO: 151 |
| miR517a | hsa-miR-517a-AUCGUGCAUCCCUUUAGAGUGU - SEQ ID NO: 152 |
| miR518f* | hsa-miR-518f*-CUCUAGAGGGAAGCACUUUCUC - SEQ ID NO: 153 |
| miR519d | hsa-miR-519d-CAAAGUGCCUCCCUUUAGAGUG - SEQ ID NO: 154 |
| miR519e | hsa-miR-519e-AAGUGCCUCCUUUUAGAGUGUU - SEQ ID NO: 155 |
| miR520a | hsa-miR-520a-3p-AAAGUGCUUCCCUUUUGGACUGU - SEQ ID NO: 156 |
| miR520a* | hsa-miR-520a*-AAAGUGCUUCCCUUUGGACUGU - SEQ ID NO: 156 |
| miR520e | hsa-miR-520e-AAAGUGCUUCCUUUUUGAGGG - SEQ ID NO: 157 |
| miR520g/h | hsa-miR-520g-ACAAAGUGCUUCCCUUUAGAGUGU - SEQ ID NO: 158 // hsa-miR-520h-ACAAAGUGCUUCCCUUUAGAGU - SEQ ID NO: 159 |
| miR555 | hsa-miR-555-AGGGUAAGCUGAACCUCUGAU - SEQ ID NO: 224 |
| miR509 | hsa-miR-509-3-5p-UACUGCAGACGUGGCAAUCAUG - SEQ ID NO: 160 |
| | hsa-miR-509-3p-UGAUUGGUACGUCUGUGGGUAG – preferred - SEQ ID NO: 161 |
| miR514 | hsa-miR-514-AUUGACACUUCUGUGAGUAGA - SEQ ID NO: 162 |
| miR515-5p | hsa-miR-515-5p-UUCUCCAAAAGAAAGCACUUUCUG - SEQ ID NO: 204 |
| miR516-3p | has-miR-516a-3p-UGCUUCCUUUCAGAGGGU - SEQ ID NO: 163 |
| miR517* | hsa-miR-517*-CCUCUAGAUGGAAGCACUGUCU - SEQ ID NO: 128 |
| miR518a | hsa-miR-518a-5p-CUGCAAAGGGAAGCCCUUUC - SEQ ID NO: 164 |
| | hsa-miR-518a-3p-GAAAGCGCUUCCCUUUGCUGGA – preferred - SEQ ID NO:165 |
| miR518c | hsa-miR-518c-CAAAGCGCUUCUCUUUAGAGUGU - SEQ ID NO: 166 |
| miR518e | hsa-miR-518e-AAAGCGCUUCCCUUCAGAGUG - SEQ ID NO: 167 |
| miR519e* | hsa-miR-519e*-UUCUCCAAAAGGGAGCACUUUC - SEQ ID NO: 168 |
| miR520d | hsa-miR-520d-5p-CUACAAAGGGAAGCCCUUUC - SEQ ID NO: 169 |
| | hsa-miR-520d-3p-AAAGUGCUUCUCUUUGGUGGGU - SEQ ID NO: 170 |
| miR521 | hsa-miR-521-AACGCACUUCCCUUUAGAGUGU - SEQ ID NO: 182 |
| miR524 | hsa-miR-524-3p-GAAGGCGCUUCCCUUUGGAGU - SEQ ID NO: 171 |
| miR524* | hsa-miR-524-5p-CUACAAAGGGAAGCACUUUCUC - SEQ ID NO: 172 |
| miR525* | hsa-miR-525-3p-GAAGGCGCUUCCCUUUAGAGCG - SEQ ID NO: 209 |
| miR526a | hsa-miR-526a-CUCUAGAGGGAAGCACUUUCUG - SEQ ID NO: 173 |
| miR549 | hsa-miR-549-UGACAACUAUGGAUGAGCUCU - SEQ ID NO: 174 |
| miR558 | hsa-miR-558-UGAGCUGCUGUACCAAAAU - SEQ ID NO: 225 |
| miR578 | hsa-miR-578-CUUCUUGUGCUCUAGGAUUGU - SEQ ID NO: 175 |
| miR611 | hsa-miR-611-GCGAGGACCCCUCGGGGUCUGAC - SEQ ID NO: 176 |

FIG. 3

Table 4: Small non-coding RNAs as marker for vaginal secretions

| miRNA | Human miRNAs |
|---|---|
| miR34a | hsa-miR-34a-UGGCAGUGUCUUAGCUGGUUGU - SEQ ID NO: 177 |
| miR124a | has-miR-124a-UAAGGCACGCGGUGAAUGCC - SEQ ID NO: 178 |
| miR195 | hsa-miR-195-UAGCAGCACAGAAAUAUUGGC - SEQ ID NO: 50 |
| miR372 | hsa-miR-372-AAAGUGCUGCGACAUUUGAGCGU - SEQ ID NO: 179 |
| miR502 | hsa-miR-502-3p-AAUGCACCUGGGCAAGGAUUCA - SEQ ID NO: 180 |
|  | hsa-miR-502-5p-AUCCUUGCUAUCUGGGUGCUA – preferred - SEQ ID NO: 181 |
| miR521 | hsa-miR-521-AACGCACUUCCCUUUAGAGUGU - SEQ ID NO: 182 |
| miR568 | hsa-miR-568-AUGUAUAAAUGUAUACACAC - SEQ ID NO: 183 |
| miR575 | hsa-miR-575-GAGCCAGUUGGACAGGAGC - SEQ ID NO: 184 |

FIG. 4

Table 5: Small non-coding RNAs as marker for salvia

| miRNA | Human miRNAs |
|---|---|
| miR10a | hsa-miR-10a-UACCCUGUAGAUCCGAAUUUGUG - SEQ ID NO: 185 |
| miR137 | hsa-miR-137-UUAUUGCUUAAGAAUACGCGUAG - SEQ ID NO: 186 |
| miR205 | hsa-miR-205-UCCUUCAUUCCACCGGAGUCUG - SEQ ID NO: 187 |
| miR206 | hsa-miR-206-UGGAAUGUAAGGAAGUGUGUGG - SEQ ID NO: 188 |
| miR208 | hsa-miR-208a-AUAAGACGAGCAAAAAGCUUGU – preferred - SEQ ID NO: 189 |
|  | hsa-miR-208b-AUAAGACGAACAAAAGGUUUGU - SEQ ID NO: 190 |
| miR216 | hsa-miR-216b-AAAUCUCUGCAGGCAAAUGUGA - SEQ ID NO: 191 |
|  | hsa-miR-216a-UAAUCUCAGCUGGCAACUGUGA – preferred - SEQ ID NO: 192 |
| miR302a | hsa-miR-302a-UAAGUGCUUCCAUGUUUUGGUGA - SEQ ID NO: 193 |
| miR302b* | hsa-miR-302b*-ACUUUAACAUGGAAGUGCUUUC - SEQ ID NO: 194 |
| miR302c | hsa-miR-302c-UAAGUGCUUCCAUGUUUCAGUGG - SEQ ID NO: 195 |
| miR302c* | hsa-miR-302c*-UUUAACAUGGGGGUACCUGCUG - SEQ ID NO: 196 |
| miR346 | hsa-miR-346-UGUCUGCCCGCAUGCCUGCCUCU - SEQ ID NO: 197 |
| miR383 | hsa-miR-383-AGAUCAGAAGGUGAUUGUGGCU - SEQ ID NO: 198 |
| miR498 | hsa-miR-498-UUUCAAGCCAGGGGGCGUUUUC - SEQ ID NO: 199 |
| miR499 | hsa-miR-499-5p-UUAAGACUUGCAGUGAUGUUU – preferred - SEQ ID NO: 200 |
|  | hsa-miR-499-3p-AACAUCACAGCAAGUCUGUGCU - SEQ ID NO: 201 |
| miR509 | has-miR-509-3p-UGAUUGGUACGUCUGUGGGUAG - SEQ ID NO: 202 |
| miR510 | hsa-miR-510-UACUCAGGAGAGUGGCAAUCAC - SEQ ID NO: 203 |
| miR515-5p | hsa-miR-515-5p-UUCUCCAAAAGAAAGCACUUUCUG - SEQ ID NO: 204 |
| miR518c* | hsa-miR-518c*-UCUCUGGAGGGAAGCACUUUCUG - SEQ ID NO: 205 |
| miR519b | hsa-miR-519b-3p-AAAGUGCAUCCUUUUAGAGGUU – preferred - SEQ ID NO: 206 |
|  | hsa-miR-519b-5p-CUCUAGAGGGAAGCGCUUUCUG - SEQ ID NO: 207 |
| miR520d | hsa-miR-520d-3p-AAAGUGCUUCUCUUUGGUGGGU - SEQ ID NO: 170 |
|  | hsa-miR-520d-5p-CUACAAAGGGAAGCCCUUUC - SEQ ID NO: 169 |
| miR525 | hsa-miR-525-5p-CUCCAGAGGGAUGCACUUUCU – preferred - SEQ ID NO: 208 |
|  | hsa-miR-525-3p-GAAGGCGCUUCCCUUUAGAGCG – SEQ ID NO: 209 |
| miR526b | has-miR-526b-CUCUUGAGGGAAGCACUUUCUGU – SEQ ID NO: 210 |
| miR548b | hsa-miR-548b-3p-CAAGAACCUCAGUUGCUUUUGU – preferred – SEQ ID NO: 211 |
|  | hsa-miR-548b-5p-AAAAGUAAUUGUGGUUUUGGCC - SEQ ID NO: 212 |
| miR551a | hsa-miR-551a-GCGACCCACUCUUGGUUUCCA - SEQ ID NO: 213 |
| miR553 | hsa-miR-553-AAAACGGUGAGAUUUUGUUUU - SEQ ID NO: 214 |
| miR577 | hsa-miR-577-UAGAUAAAAUAUUGGUACCUG - SEQ ID NO: 215 |
| miR600 | hsa-miR-600-ACUUACAGACAAGAGCCUUGCUC - SEQ ID NO: 216 |
| miR604 | hsa-miR-604-AGGCUGCGGAAUUCAGGAC - SEQ ID NO: 217 |
| miR606 | hsa-miR-606-AAACUACUGAAAAUCAAAGAU - SEQ ID NO: 218 |
| miR643 | hsa-miR-643-ACUUGUAUGCUAGCUCAGGUAG - SEQ ID NO: 219 |
| miR647 | hsa-miR-647-GUGGCUGCACUCACUUCCUUC - SEQ ID NO: 220 |
| miR658 | hsa-miR-658-GGCGGAGGGAAGUAGGUCCGUUGGU - SEQ ID NO: 221 |
| miR802 | hsa-miR-802-CAGUAACAAAGAUUCAUCCUUGU - SEQ ID NO: 222 |
| miR516-5p | hsa-miR-516a-5p-UUCUCGAGGAAAGAAGCACUUUC - SEQ ID NO: 223 |
| miR555 | hsa-miR-555-AGGGUAAGCUGAACCUCUGAU - SEQ ID NO: 224 |
| miR558 | hsa-miR-558-UGAGCUGCUGUACCAAAAU - SEQ ID NO: 225 |
| miR569 | hsa-miR-569-AGUUAAUGAAUCCUGGAAAGU - SEQ ID NO: 226 |
| miR587 | hsa-miR-587-UUUCCAUAGGUGAUGAGUCAC - SEQ ID NO: 227 |

FIG. 5

METHOD FOR DETERMINING THE ORIGIN OF A SAMPLE

CROSS-REFERENCE TO RELATED APPLICATIONS

The present application is a U.S. National Stage Application under 35 U.S.C. §371 of International Patent Application No. PCT/EP2009/005254, filed Jul. 20, 2009, which claims benefit of U.S. Provisional Patent Application No. 61/082,056, filed Jul. 18, 2008.

SEQUENCE LISTING

The instant application contains a Sequence Listing which has been submitted via EFS-Web and is hereby incorporated by reference in its entirety. Said ASCII copy, created on Jan. 18, 2011, is named Sequence_listing.txt and is 33,798 byte in size.

The present application pertains to methods and kits for determining the nature (e.g. origin) of a sample, e.g. a body fluid. The teaching of the present application is particularly useful in the field of human identity testing, paternity testing or forensic science (forensics).

The application of DNA technology to the biological evidence in criminal casework has revolutionized forensic science. The ability to identify, with a high degree of certainty, a suspect in violent crimes now routinely provides valuable leads to criminal investigators worldwide, often in circumstances where there are no eyewitnesses. Forensic DNA technology or STR-typing is a very sensitive and universally accepted scientific technique. STRs are small DNA regions that contain DNA segments that repeat several times in tandem. Repeated sequences are a fundamental feature of genomes and play an important role in genomic fingerprinting (for review see Jobling and Gill, Nature Reviews in Genetics, Vol. 5, pp 739; 2004).

Human identity DNA testing involves generating information on the size and number of certain repetitive sequences. This information resembles the unique pattern of a fingerprint and is thus often referred to as the "genetic fingerprint" of a human individual. Genetics fingerprints may be compared with each other in a database system and allow for positive identification of an individual.

However, genetic fingerprints do not reveal any information on the physical appearance of the human donor—except for the sex—or the specific nature and origin of the human sample. However, such information is very useful in criminal investigation as it can make a decisive difference whether a sample obtained from the clothing of a sexual assault victim is a droplet of sperm or saliva, or whether blood sampled from some female underwear is peripheral or menstrual blood.

Conventional methods for the identification of different body fluids like blood, semen and saliva from biological stains involve immunological or enzymatic detection of certain proteins, which are characteristic for the respective sample. However, these technologies (e.g. ELISA, lateral flow chromatography) are often not sensitive enough for forensic investigation as proteins cannot be amplified and forensic stains often contain only minute amounts of materials.

Typically, such conventional methods for body fluid stain analysis are carried out in a serial manner, with a portion of the stain being tested for only one body fluid at a time. Frequently multiple tests are required to first presumptively identify the presence of biological fluids followed by additional testing in order to confirm the presence of the fluid or identify the species of origin. Therefore these methods are costly not only in the time and labor required for their completion, but also in terms of the amount of sample consumed during the performance of each assay. While these conventional methods can confirm the presence of human blood and semen, none of the routinely used serological and immunological tests can definitely identify the presence of human saliva or vaginal secretions. With the large volume of cases that operational crime laboratories are faced with processing every year, a significant amount of the total time spent on an individual case can be devoted solely to the screening of evidentiary items for the presence of biological materials. The inability to positively confirm the presence of certain biological fluids, the consumption of valuable samples and the time and labour required has resulted in a trend to bypass conventional body fluid identification methods and proceed straight to the analysis of DNA present in forensic samples.

There are several disadvantages to bypassing the body fluid identification step during bio-molecular forensic analysis. First, the analytical methods used to analyze DNA are considerably more expensive than basic serological testing. A second disadvantage of the disuse of body fluid identification methods is that often the identification of the biological material present is crucial to the investigation and prosecution of the case.

The routine use of body fluid identification methods prior to DNA analysis awaits the development of suitable molecular genetics based methods that are fully compatible with the current DNA analysis pipeline. In order for any new body fluid assay to be suitable for forensic casework it must demonstrate a high degree of specificity for each body fluid, permit parallel analysis of the different biological fluids, be completed in a timely and labour efficient manner and must be sufficiently sensitive.

It is thus the object of the present invention to provide a method which allows determining the nature of a sample, such as a forensic sample.

BRIEF DESCRIPTION OF THE DRAWINGS

FIG. 1 shows Table 1 which depicts suitable miRNAs which are useful markers for blood.

FIG. 2 shows Table 2 which depicts suitable miRNAs which are useful markers for menstrual blood.

FIG. 3 shows Table 3 which depicts suitable miRNAs which arc useful markers for semen.

FIG. 4 shows Table 4 which depicts suitable miRNAs which are useful markers for vaginal secretions FIG. 5 shows Table 5 which depicts suitable miRNAs which are useful markers for saliva.

Figure 6:
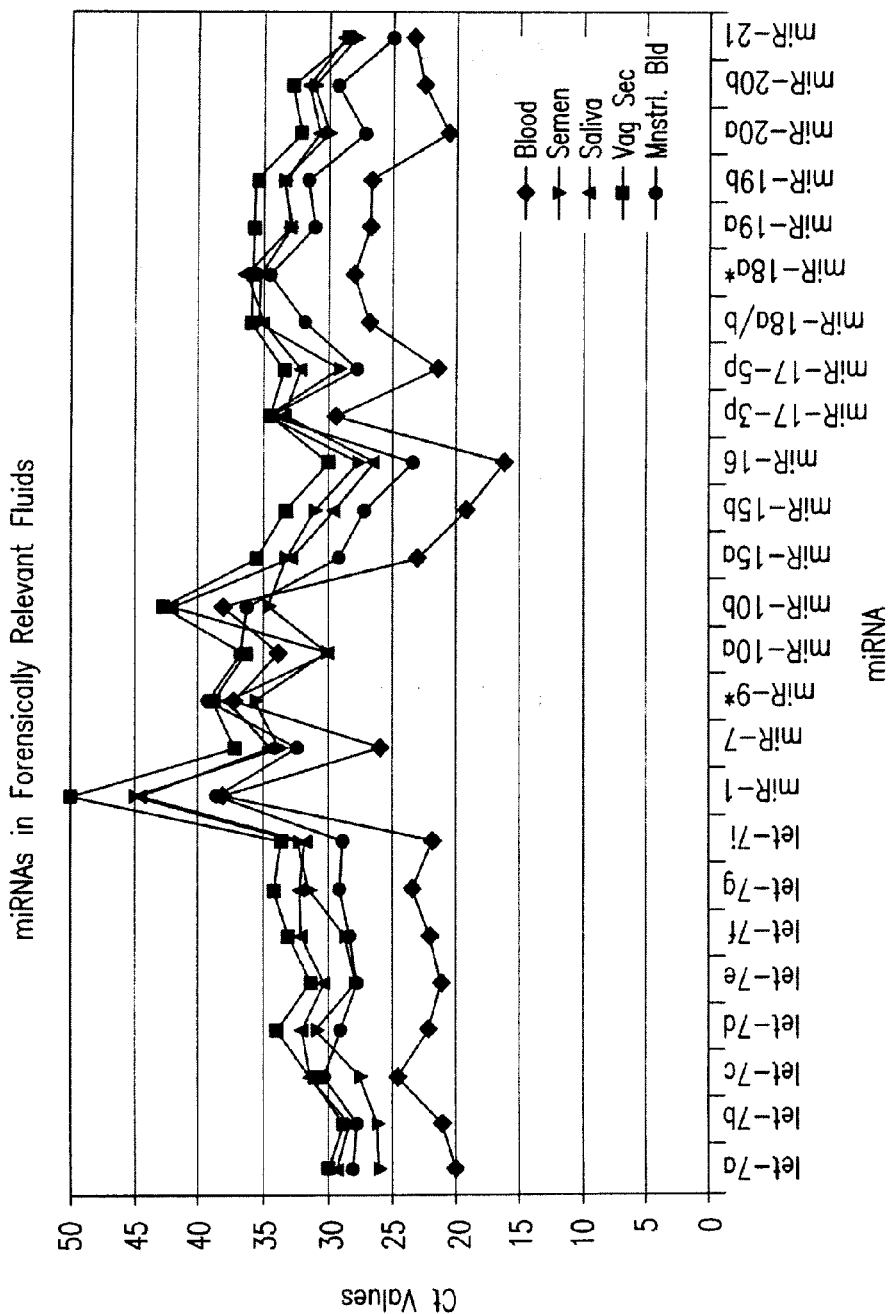
FIG. 6 shows the results of a miRNA candidate screening using pooled body fluid samples.
Figure 7A:
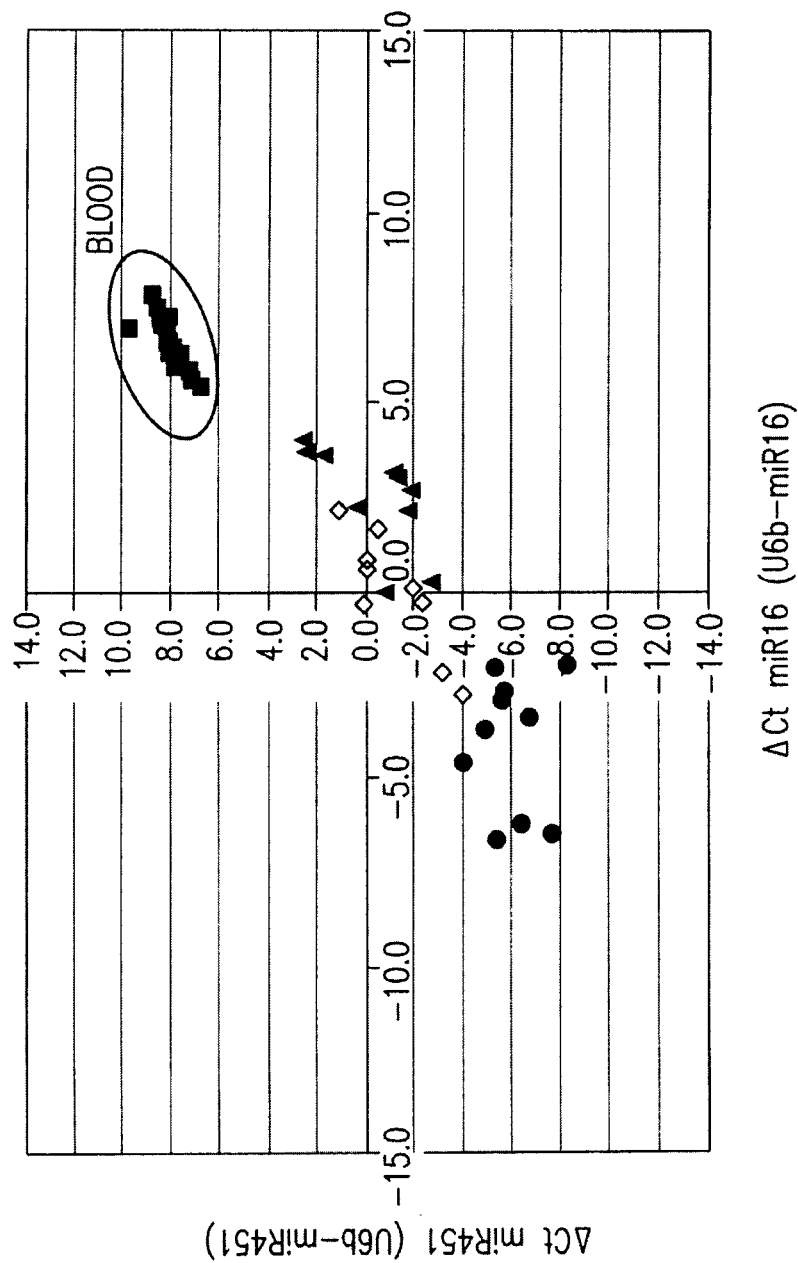
FIG. 7A-7E show the development of 2-1) miRNA body fluid identification assays.
Figure 7B:
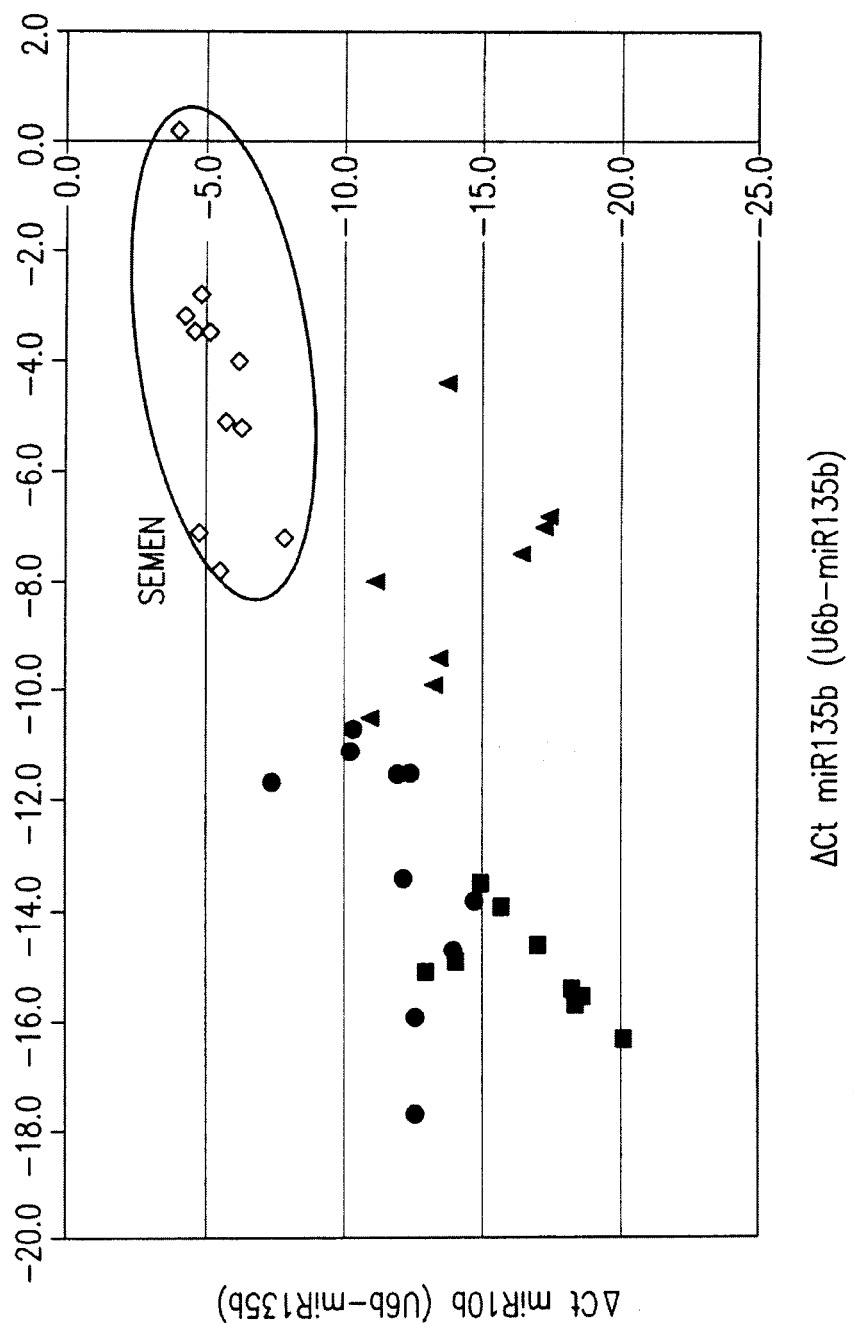
Figure 7C:
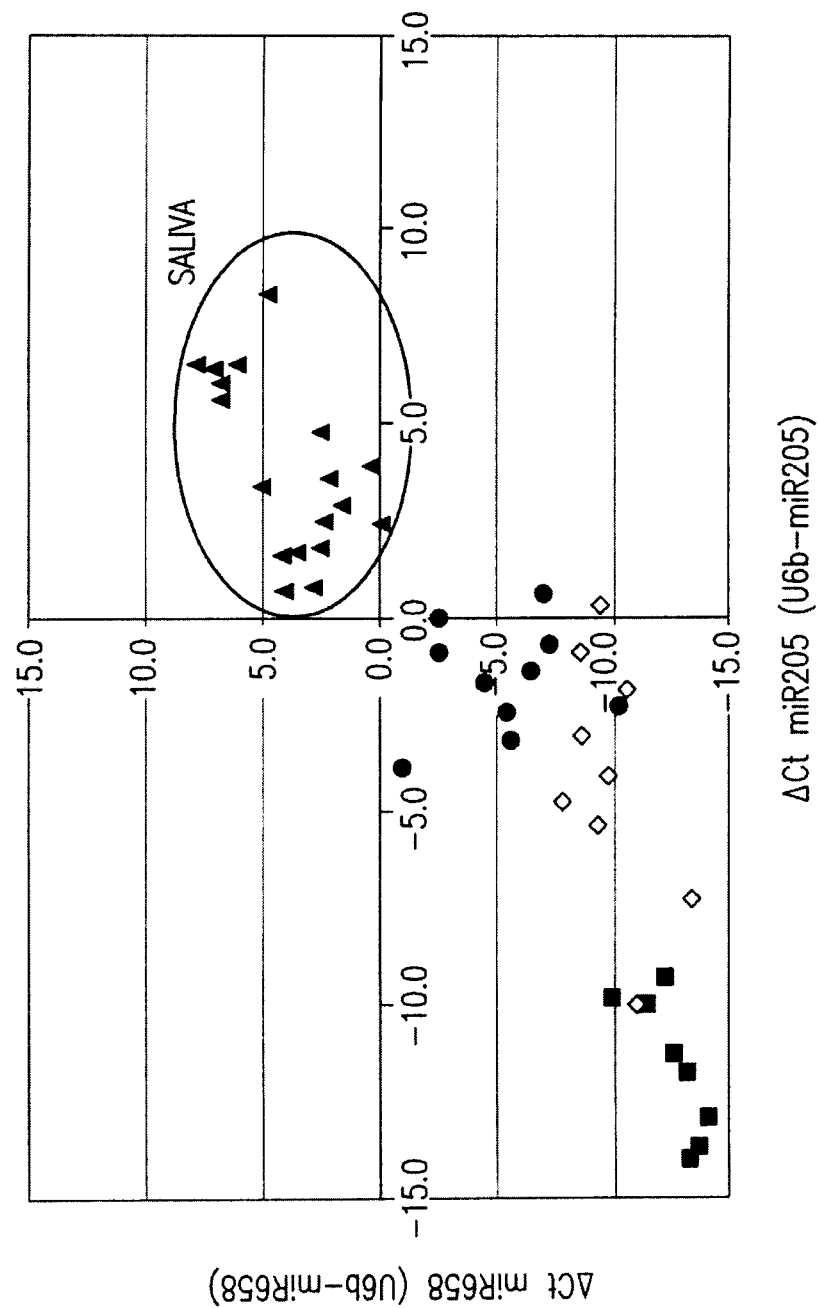
Figure 7D:
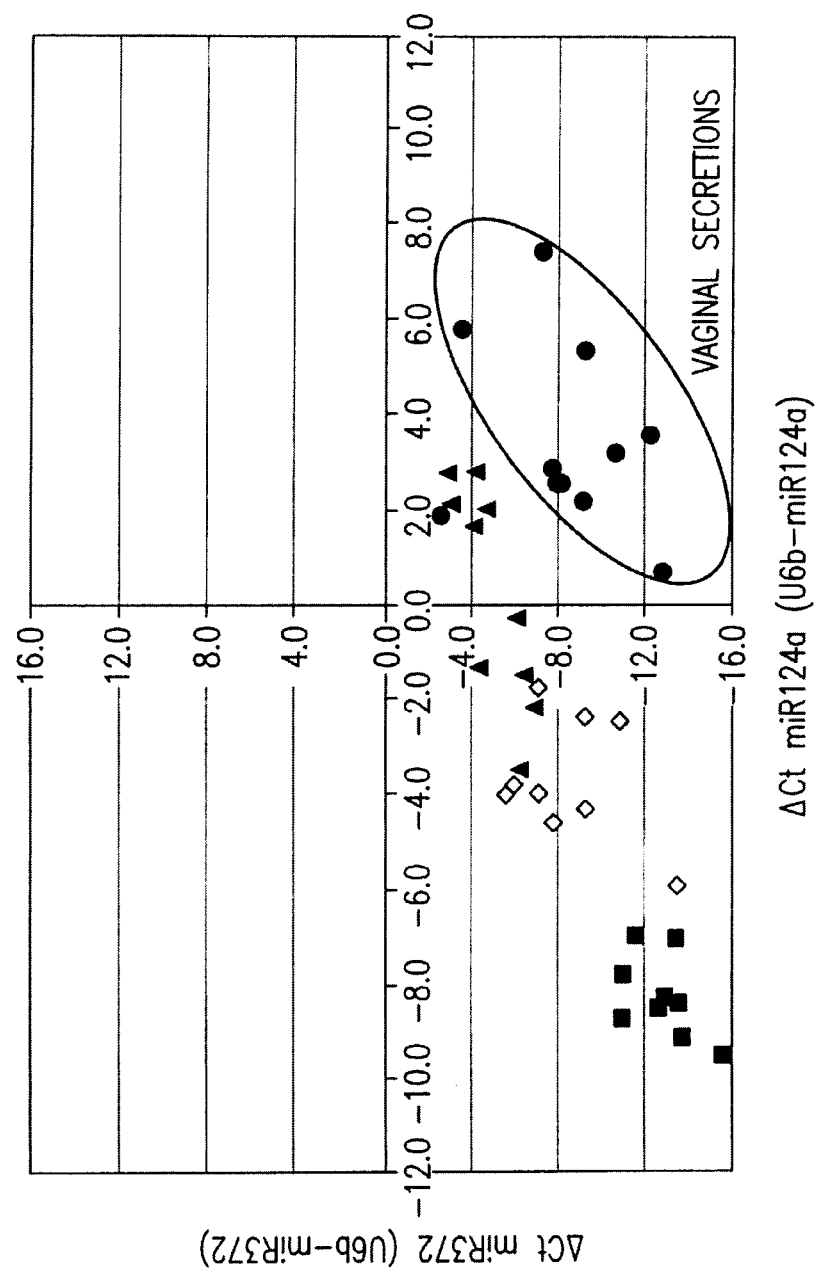
Figure 7E:
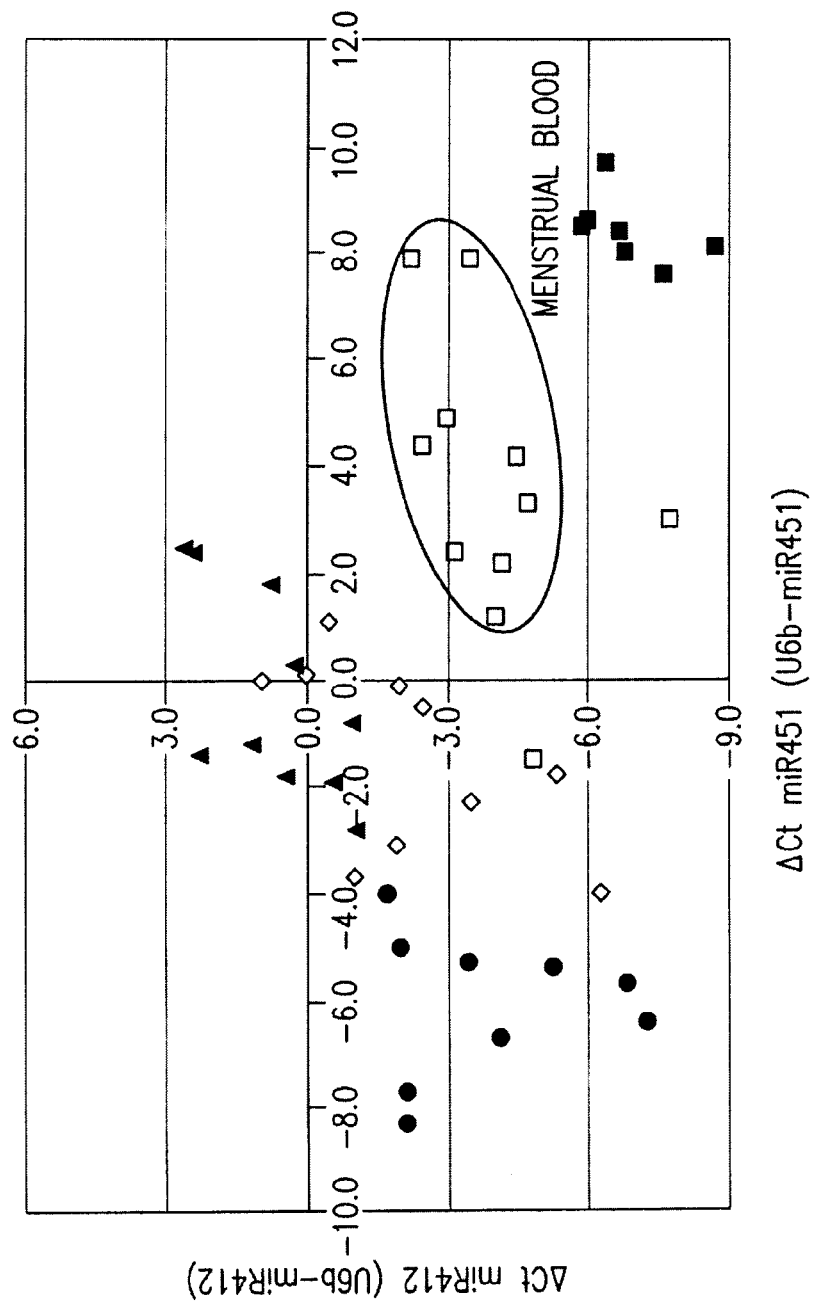

According to one embodiment, a method for determining the nature of a sample is provided, wherein the presence or absence of at least one marker small non-coding RNA in the sample is detected. The detection of a respective marker small non-coding RNA allows the identification of the nature of the sample, such as e.g. its origin or type. The analysis/detection of the expression of at least one small non-coding RNA is advantageous over conventional detection methods which e.g. target mRNA, which is likely to be more susceptible to degradation and expected to be less stable due to its larger size. It is also advantageous over the detection of marker proteins due to the reasons outlined above. However, respective methods can also be used in combination with the method of the present invention.

Several small non-coding RNAs (ncRNAs) are known in the prior art. They comprise infrastructural ncRNAs such as, for example, tRNAs, rRNAs, spliceosomal uRNAs or snRNAs and the common snoRNAs. Both translation and splicing require core infrastructural RNAs not only for sequence-specific recognition of RNA substrates, but also for the catalytic process itself. A further category of small non-coding RNAs comprises small regulatory ncRNAs such as snoRNAs and miRNAs/siRNAs.

snoRNAs generally range from 50 to 300 nucleotides in length and guide the side-specific modification of nucleotides and target RNAs via short regions of base paring. There are two major classes, the box C/D snoRNAs which guide 2'-O-ribose-metylation and the box H/ACA snoRNAs which guide pseudouridylation of target RNAs. At least some snoRNAs exhibit tissue-specific and developmental regulation and/or imprinting, indicative of a regulatory function.

miRNAs and siRNAs are short, approximately less than 30 and usually around 22 nucleotides long RNA molecules derived either from hairpin or double stranded RNA precursors. Details of miRNA and siRNA biology and their biochemistry are known in the prior art. miRNAs suppress translation via non-perfect pairing with target mRNAs—usually involving a seed pairing of just 6-8 nucleotides in length or (as with siRNAs) cause degradation of target RNAs via the RISC complex in the case of perfect complementarily with the target site—the phenomenon known as RNAi. It is estimated that approximately ⅓ of human protein-coding genes are controlled by miRNAs. In addition, siRNAs derived from repeats participate in the establishment of silenced (heterochromatic) chromatin, as well as in other aspects of chromosome dynamics. miRNAs are derived from the introns and exons of both protein-coding and non-coding transcripts that are synthesised by RNA polymerase II. It has recently been shown that a number of mammalian miRNAs are derived from repeats, mainly various transposons. Some miRNAs also appear to be derived from processed pseudo genes.

An overview over small non-coding RNAs, their structure and function is described in John S. Mattick and Igor V. Makunin: Non-coding RNA, Human Molecular Genetics 2006, Volume 15, review issue 1 R17-R29, herein fully incorporated by reference.

According to one embodiment the small non-coding RNA is a miRNA. In the last few years, the identification of microRNA (miRNA) and the recognition of its important role in regulation of gene expression have led to increasing interest in the identification and characterization of miRNAs (Cummins, J. M. and Velculescu, V. E. (2006) Implications of micro-RNA profiling for cancer diagnosis. Oncogene 25, 6220; microRNAs supplement (2006) Nature Genetics 38, 6s; Kloosterman, W. P. and Plasterk, R. H. (2006) The diverse functions of microRNAs in animal development and disease. Dev. Cell 11, 441. A growing body of evidence suggests that miRNAs play a role in many diverse biological processes such as development, differentiation, and apoptosis. Misregulation of miRNA expression is reported to be associated with several cancers and other diseases. MicroRNAs (miRNAs) are small non-coding RNAs, which usually have a length of less than 30 nt, usually around 21 to 22 nt. The generation of miRNAs is also described in FIG. 9.

miRNAs and other small non-coding RNAs such as snoRNAs or piRNAs are ideal assay targets for identifying the nature of a sample, e.g. in forensic testing due to several reasons. Because of their small size they are generally expected to be more stable than larger RNA species and in particular mRNA. In addition they are typically expressed at very high rates. Thus, they potentially can also be recovered from older samples what is of particular importance in the field of forensics. Furthermore, their regulatory function in gene expression during human development and tissue differentiation suggests the potential for identification of specific miRNA species that are indicative of the nature of a sample or even the donor's physical status such as age or health. To date more than 500 different individual miRNA and other small RNAs have been identified in humans. The identification of miRNAs which are specifically expressed in a particular sample type provides a valuable marker for sample typing.

According to one embodiment, the presence or absence of at least two marker small-non-coding RNAs in the sample is detected in order to determine the nature of the sample. To characterise the sample type (e.g. to determine whether a sample is semen or saliva) by using at least two sample specific markers provides more security during testing and allows a more reliable interpretation/control of the results.

A specifically suitable marker small non-coding RNA has at least one of the following characteristics:
 a. It is expressed in the particular sample for which the small non-coding RNA serves as marker;
 b. it shows a discriminating/differential expression pattern in a particular type of sample compared to other sample types;
 c. it is specifically expressed in a particular sample type; and/or
 d. it is expressed in higher abundance in a particular sample type.

A respective expression pattern which is characteristic for a particular sample type and differs from the expression pattern in other (either all, or at least some) sample types ensures sufficient specificity for the sample type for which the respective small non-coding RNA is used as a marker. Appropriate differentiation of the expression in the particular type of sample compared to other samples is important in order to enhance the specificity of the determination method. It is advantageous to use a marker small non-coding RNA which is expressed in the particular sample. This, as the detection of an expression ensures that the assay worked properly. In case a marker small non-cording RNA is used whose characteristic is that it is not expressed in a certain sample type, there is always a certain risk/doubt that the method/assay did not work properly which would need to be ensured by using appropriate controls. The use of a high-abundance small non-coding RNA over a low-abundance small non-coding RNA is generally preferred, as the expression of a high-abundance marker is easier to detect.

Typical sample types that play an important role in particular in the field of forensics are e.g. blood, menstrual blood, semen, vaginal secret and saliva. The method of the present invention allows a reliable identification/determination of the type of the respective sample by detecting/analysing the expression pattern of respective marker small non-coding RNAs. The detection of the expression of a specific marker or a certain marker profile characteristic for the specific sample allows the identification of the nature/origin of the sample (e.g. whether it is semen or saliva). It is also within the scope of the present invention to detect the presence or absence of a plurality of small non-coding RNAs indicative as markers for a plurality of different sample types, and determining the nature of the sample based on the obtained expression profile for the respective markers. E.g. in case a sample is collected at a forensic scene that could be blood, one could simultaneously or consecutively perform the method of the present application by analysing the expression of marker small non-coding RNAs for blood and menstrual blood. Depending on the obtained expression profile, one would obtain the information whether the collected sample is peripheral blood or menstrual blood. The principle is also valid for other sample types such as the ones mentioned above. The marker small non-coding RNAs for different tissues may also be tested in parallel and thus in one assay thereby allowing the typing of the unidentified sample.

For detecting the marker small non-coding RNA in the sample, any detection method can be used. It is preferred that the detection method also allows a quantification of the detected marker small non-coding RNA in the sample. Hence, the detection is preferably quantitative. Non-limiting examples of suitable detection methods are amplification, PCR, real time PCR, e.g. using SybrGreen or probes, isothermal amplification reactions, sequencing reactions, in particular pyrosequencing and massive parallel high throughput sequencing (for example 454 sequencing, Applied Biosystems SOLID which also allows a quantification), detection based on hybridisation techniques, e.g. via microarrays, chips, bead arrays, functionalised surfaces, e.g. using microtiter plates, and detection via high resolution melt curve analysis. The detection may comprise the use of labelled probes/oligonucleotides, for example fluorescently labelled oligonucleotides or amplification products. Other detectable signals are based e.g. on chemiluminescence, radioactivity or electrochemical processes. Several suitable detection methods are known in the prior art that can be used in conjunction with the present invention which thus do not need to be described in detail herein. Suitable methods are also described in WO 2008/020008, herein incorporated by reference.

According to one embodiment, at least one small non-coding RNA is detected which comprises or consists of a sequence selected from the group of small non-coding RNAs listed in Table 1 (see FIG. 1) or is an isoform thereof (having no more than 5, preferably no more than 3 or more preferred no more than 2 base changes) or is derived from the same premiRNA as the respective small non-coding RNAs listed in Table 1 (see FIG. 1), as a marker for blood, in particular peripheral blood. The respective miRNAs are specifically/differentially expressed in blood samples and are thus suitable markers for determining/identifying an unknown sample as a blood sample. Suitable sequence specific oligonucleotides and probes that are useful for amplifying and/or detecting the corresponding marker miRNAs can be designed applying known principles e.g. based on the shown sequence of the miRNA; sequence specific oligonucleotides and probes should be at least 80% homologous, preferably at least 90% complementary to the target sequence to allow sequence specific detection. It is advantageous that at least two small non-coding RNAs are selected from the following group of small non-coding RNAs as markers for blood:

Let7i
miR15a
miR15b
miR16
miR106a
miR106b
miR126
miR182 miR182*
miR185
miR190
miR195
miR374
miR451
miR545
miR624
miR627
miR154*
miR607

It was demonstrated in extensive experiments by the inventors that the respective miRNAs are useful markers for blood, particularly peripheral blood, which thus allow the secure identification/determination of an unknown sample as a respective blood sample. Particularly advantageous are the use of Let7i, miR16, miR451, and/or miR15b as specific markers. Preferably, at least miR451 and miR16 are used as a marker pair respectively marker combination for typing peripheral blood samples.

In addition or alternatively, at least one small non-coding RNA is detected which comprises or consists of a sequence selected from the group of small non-coding RNAs listed in Table 2 (see FIG. 2) or is an isoform thereof (having no more than 5, preferably no more than 3 or more preferred no more than 2 base changes) or is derived from the same premiRNA as the respective small non-coding RNAs listed in Table 2 (see FIG. 2), as a marker for menstrual blood. The respective miRNAs are specifically/differentially expressed in blood samples and in particular in menstrual blood samples and are thus suitable markers for determining/identifying an unknown sample as a menstrual blood sample. Suitable sequence specific oligonucleotides and probes that are useful for amplifying and/or detecting the corresponding marker miRNAs can be designed applying known principles e.g. based on the shown sequence of the miRNA; sequence specific oligonucleotides and probes should be at least 80% homologous, preferably more than 90% complementary to the target sequences to allow sequence specific detection. It is advantageous that at least two small non-coding RNAs are selected from the following group of small non-coding RNAs as markers:

miR23a/b
miR33
miR95
miR106b
miR154
miR218
miR369-5p
miR377
miR412
miR423
miR425-3p
miR451
miR452
miR452*
miR484
miR494
miR648
miR369-5p
miR507
miR648

Particularly suitable are the detection of the following miRNAs as markers for menstrual blood: miR451, miR423, miR484, miR412, miR425-3p and/or miR452*. It was demonstrated in extensive experiments by the inventors that the respective miRNAs are useful markers for menstrual blood which thus allow the secure identification/determination of an unknown sample as a menstrual blood sample even compared to a peripheral blood sample. Particularly suitable is the use of at least miR412 and miR451 as marker pair respectively combination for typing menstrual blood samples. The respective markers also allow a differentiation between menstrual blood and peripheral blood samples.

The detection of menstrual blood markers in combination with general and/or peripheral blood markers (see above) is particularly useful for a blood/menstrual blood assay. As the menstrual blood markers also show a differential expression pattern in peripheral blood compared to menstrual blood, they can also be used in order to distinguish peripheral blood from menstrual blood samples.

In addition or alternatively, at least one small non-coding RNA is detected which comprises or consists of a sequence selected from the group of small non-coding RNAs listed in Table 3 (see FIG. 3) or is an isoform thereof (having no more than 5, preferably no more than 3 or more preferred no more than 2 base changes) or is derived from the same premiRNA as the respective small non-coding RNAs listed in Table 3 (see FIG. 3), as a marker for semen. The respective miRNAs are specifically/differentially expressed in semen samples and are thus suitable markers for determining/identifying an unknown sample as a semen sample. Suitable sequence specific oligonucleotides and probes that are useful for amplifying and/or detecting the corresponding marker miRNAs can be designed applying known principles e.g. based on the shown sequence of the miRNA; sequence-specific oligonucleotides and probes should be at least 80% homologous, preferably at least 90% complementary to the target sequences to allow sequence-specific detection. It is advantageous that at least two small non-coding RNAs are selected from the following group of small non-coding RNAs as markers for semen:

| |
|---|
| miR10b |
| miR99a |
| miR135a |
| miR135b |
| miR204 |
| miR508 |
| miR513 |
| miR517a |
| miR518f* |
| miR519d |
| miR520a* |
| miR520g/h |
| miR514 |
| miR518c |
| miR518e |
| miR524* |
| miR611 |

It was demonstrated in extensive experiments by the inventors that the respective miRNAs are particularly useful markers for semen which thus allow the secure identification/determination of an unknown sample as a semen sample. Particularly suitable are the detection of the following miRNAs as markers for semen: miR10b, miR135b, miR517a, miR508, miR514, miR520g/h and/or miR204. Particularly suitable is the use of at least miR135b and miR10b as marker pair respectively marker combination for typing/identifying semen samples.

Alternatively or additionally, at least one small non-coding RNA is detected which comprises or consists of a sequence selected from the group of small non-coding RNAs listed in Table 4 (see FIG. 4) or is an isoform thereof (having no more than 5, preferably no more than 3 or more preferred no more than 2 base changes) or is derived from the same premiRNA as the respective small non-coding RNAs listed in Table 4 (see FIG. 4), as a marker for vaginal secretions. The respective miRNAs are specifically/differentially expressed in vaginal secretion samples and are thus suitable markers for determining/identifying an unknown sample as a vaginal secretion sample. Suitable sequence specific oligonucleotides and probes that are useful for amplifying and/or detecting the corresponding marker miRNAs can be designed applying known principles e.g. based on the shown sequence of the miRNA, oligonucleotides shall be at least 80% homologous, preferably at least 90% complementary to the target sequences to allow sequence specific detection. It is advantageous that at least two small non-coding RNAs are selected from the following group of small non-coding RNAs as markers for vaginal secretion samples:

| |
|---|
| miR124a |
| miR195 |
| miR372 |
| miR521 |
| miR568 |

It was demonstrated in extensive experiments by the inventors that the respective miRNAs are particularly useful markers for vaginal secretions which thus allow the secure identification/determination of an unknown sample as a vaginal secretion sample. Particularly suitable are the detection of the following miRNAs as markers for vaginal secretions: miR124a, miR195, and/or miR372. Particularly suitable is the use of at least miR124a, miR372, and miR195 as marker pair respectively marker combination for typing/identifying vaginal secretion samples.

Additionally or alternatively, at least one small non-coding RNA is detected which comprises or consists of a sequence selected from the group of small non-coding RNAs listed in Table 5 (see FIG. 5) or is an isoform thereof (having no more than 5, preferably no more than 3 or more preferred no more than 2 base changes) or is derived from the same premiRNA as the respective small non-coding RNAs listed in Table 5 (see FIG. 5), as a marker for saliva. The respective miRNAs are specifically/differentially expressed in saliva samples and are thus suitable markers for determining/identifying an unknown sample as a saliva sample. Suitable sequence specific oligonucleotides and probes that are useful for amplifying and/or detecting the corresponding marker miRNAs can be designed applying known principles e.g. based on the shown sequence of the miRNA. It is advantageous that at least two small non-coding RNAs are selected from the following group of small non-coding RNAs as markers for saliva:

| |
|---|
| miR205 |
| miR206 |
| miR208 |
| miR302c |
| miR509 |
| miR510 |
| miR515-5p |
| miR518c* |
| miR525 |
| miR526b |
| miR551a |
| miR600 |
| miR606 |
| miR555 |
| miR587 |
| miR658 |

It was demonstrated in extensive experiments by the inventors that the respective miRNAs are particularly specific markers for saliva which thus allow the secure identification/determination of an unknown sample as a saliva sample. Particularly suitable are the detection of the following miRNAs as markers for saliva: miR658, miR606, miR510, miR526b, miR208 and/or miR205. Particularly suitable is the use of at least miR658 and miR205 as marker pair respectively marker combination for typing/identifying saliva samples. It was demonstrated in extensive experiments by the inventors that the respective miRNAs are particularly useful markers for saliva which thus allows the secure identification/determination of an unknown sample as a saliva sample.

The success and accuracy of any biological assay involving the use of quantitative expression analysis often also depends on proper normalization of data. The purpose of normalization is to minimize potential variation that can mask or exaggerate biologically meaningful changes. Quantitative assessments of total RNA in a sample can be affected by various factors including extraction efficiencies of RNA from different body fluids and substrates upon which they were deposited as well as potential RNA degradation. The currently available RNA quantification methods are usually not human-specific and therefore RNA quantity estimations can also be affected by the presence of contaminating non-human species. Potential normalization strategies for use in miRNA expression analysis include the use of housekeeping genes (mRNA), small RNAs such as 5S rRNA or U6b (a small nucleolar RNA), and universally expressed miRNAs. Ideally, a normalizer should be present in relatively high and consistent abundance in all tissues or cell types, should be of similar size and found in similar cellular environments as the target molecule, and be compatible with the analysis methods utilized for the target molecule. Messenger RNAs from housekeeping genes may not be the most suitable targets for normalization of miRNA expression data due to abundance, degradation rates and amplimer size differences. For example, universally (and approximately) equally expressed 'housekeeping' miRNAs could be used as normalizers.

Thus, according to one embodiment, the expression of the marker small non-coding RNA is normalized relative to a generically expressed small non-coding RNA which can be of the same or a different type than the marker sample. This allows a relative quantification of the marker small non-coding RNA and hence ensures a reliable detection independent of extraction efficiency and sample preservation. The normalization marker may serve as a positive control at the same time. According to one embodiment, the expression of a small non-coding RNA is determined for normalisation which is different from the marker small non-coding RNA to be detected. To detect a small non-coding RNA for normalisation is advantageous as they would depict the same degradation profile/advantages as the small non-coding RNA detected as a marker for a particular sample type. The small non-coding RNA used for normalization has a Ct value close to the marker small non-coding RNA in order to simplify the comparison.

According to one embodiment, the small non-coding RNA used for normalization is selected from the group consisting of U6B, U44, S15 or miRNAs which have a similar Ct value in the samples of interest. The respective small non-coding RNAs showed good characteristics in the performed tests. Other examples include U26, U27, U28, U29, U30, U31, U38B, U43, U48 and U90. The choice of the normaliser may also be adapted to the sample type or assay as it may provide further sample specificity (see below). Also more than one normaliser may be used.

Different normalisation concepts can be used according to the present invention.

For absolute quantification, e.g. a synthetic miRNA can be used that can be mixed for more reliable handling or mimic of background nucleic acid with carrier RNA such as corn or bacterial RNA. E.g. 50 ng per RT reaction (2.5 ng/µl) of the carrier can be used. A respective approach enables maximum quantification of all steps including the reverse transcriptase step (see below) with minimum effort.

Another normalisation approach which can be used to quantify the marker small non-coding RNAs and in particular the miRNAs is the delta delta Ct method. For relative delta delta Ct quantification, assays for snoRNAs can be used. A snoRNA with a Ct value close to the marker small non-coding RNA of interest is an appropriate one as control. Alternatively, if individual expression levels are not determined, e.g. the snoRNAs U6B and U44 can be used as a general control for all small non-coding RNAs and in particular miRNAs. Small nucleolar RNAs (snoRNAs) participate in the processing and modification of other ribonucleic acids—in particular rRNA. snoRNAs do not encoded proteins but operate as "guide" RNAs, by directing catalytically active proteins to the right places/positions of the RNA. Usually, snoRNAs are in the cell associated with other proteins and form a so-called snoRNPs (small nucleolar ribonucleoprotein particle). The modifications that are introduced by the snoRNPs into the rRNAs are inter alia essential for the functions of the ribosome.

According to one embodiment, total RNA extracts are first quantitated e.g. using a RiboGreen fluorescence assay and equal amounts of total RNA are used in subsequent reverse transcription assays. However, this normalization strategy may not be sufficiently precise enough on its own for certain applications of the present technology due the potential presence of differing levels of non-human sources of RNA in some forensic samples (e.g. bacteria in saliva and vaginal secretions). Therefore, one may also employ alternatively or additionally a delta Ct (deltaCt) metric which measures the relative abundance of a particular miRNA in relation to e.g. a small nucleolar RNA, e.g. U6b or U44. U6b is advantageous due to its high abundance and apparent stability in different body fluid stains of forensic interest. For example, for high abundance miRNA candidates whose expression was greater than e.g. U6b, the deltaCt metric was obtained by subtracting the Ct value of miRNA from the Ct value of the U6b, whereas for miRNAs present in lower abundance than U6b, the deltaCt was obtained by subtracting the Ct value of e.g. U6b from the Ct value of the miRNA.

According to one embodiment, the method comprises at least one of the following steps:
 a. isolating RNA from the sample
 b. optionally quantifying the isolated RNA
 c. reverse transcribing the isolated RNA
 d. detecting, preferably amplifying, at least one marker small non-coding RNA.

The respective process steps are routine steps for the person of skill in the art and thus can be easily and routinely performed. Amplification is preferably performed by PCR in order to be able to detect the presence or absence of the marker small non-coding RNAs even in very small samples. Suitable amplification and detection methods are described above. The detection is preferably quantitative.

Isolation of the RNA is performed by using conventional methods. Preferably methods are used which allow the efficient isolation of small RNAs of e.g. less than 1000 or even 500 or 100 nucleotides from a sample. One suitable method is the standard guanidine isothiocyanate-phenol: chloroform based extraction method (see e.g. Chomczynski P, Sacchi N (1987) Single-step method of RNA isolation by acid guanidinium thiocyanate-phenol-chloroform extraction. Anal Biochem 162: 156-159). Numerous non-organic, silica-based extraction kits are now commercially available for the recovery of miRNAs and, in contrast to the phenol-chloroforms methods, are easily transferable to an automated platform. Thus these kits may prove more suitable for use in forensic casework. An appropriate amount of total RNA (e.g. ~1-5 ng) would be used for reverse transcription (RT). Several reverse transcription methods are known in the prior art that can be used in conjunction with the present invention. For reverse transcription, the isolated RNA is preferably tailed (e.g. with a poly A tail) in order to allow the reverse transcription of the small non-coding RNA by using a universal oligonucleotide/adapter recognising the tail. Amplification is performed using appropriate oligonucleotides. E.g. a sequence specific oligonucleotide for the marker small non-coding RNA of interest and a oligonucleotide recognising the tail/adapter incorporated due to the tailing/reverse transcription can be used for amplification. Suitable commercially available kits for extraction and reverse transcription are e.g. sold by QIAGEN, such as e.g. the miScript system. Unlike other commercially available miRNA systems that employ miRNA-specific reverse transcription strategies, the miScript system allows cDNA to be produced from all RNA species within the sample, including mRNAs and other small non-coding RNAs. This could be advantageous in forensic casework where multiple individual reverse transcription reactions required to analyze a sufficient amount of miRNAs may not be possible due to a limited amount of genetic material recovered from most evidentiary items.

The ability to simultaneously reverse transcribe other RNA species, such as mRNAs, may also be useful if parallel assays need to be performed for the detection of tissue specific mRNAs or housekeeping genes. Suitable methods are also described in WO 2008/020008, herein incorporated by reference. An appropriate volume of the RT product to obtain e.g. 50 pg (suitable for the blood, saliva, vaginal secretions and menstrual blood assays) or e.g. 500 pg (suitable for the semen assay) cDNA would be used in the miRNA quantitative real time PCR (QT-PCR) assay which, according to one embodiment, uses the miScript SYBR Green PCR system and a miRNA specific oligonucleotide. Suitable sequence specific oligonucleotides and probes that are useful for amplifying and/or detecting the corresponding marker small non-coding RNAs, e.g. miRNAs can be designed applying known principles based on the sequence of the marker miRNA to be detected.

According to the method/assay of the present invention, it is possible to analyse several marker small non-coding RNAs and if desired, at least one, preferably at least two, normalisers (e.g. U6b and U44) from a single RT product. Numerous RT reactions are not required for the examination of multiple marker small non-coding RNAs in the same sample. If a real-time PCR is performed, the Ct values for each marker small non-coding RNA may then be evaluated to ensure all obtained values are within acceptable ranges. All acceptable expression data can then be normalized using e.g. U6b in which the Ct value of the miRNA is subtracted from the Ct value of U6b. The delta Ct values for the at least two marker small non-coding RNAs for each sample/body fluid may then be used to position the unknown sample e.g. two-dimensional scatter plot for each body fluid. The identification of the presence of the sample/body fluid would be confirmed if the unknown sample was found within the cluster of known body fluid samples. If a positive result is obtained for e.g. blood, deltaCt values using U44 for miR451 and miR16 (preferably used in the assay) may then be calculated and used to determine the species of origin. The presence of human (or higher primate) blood would be indicated by the presence of the unknown sample within the cluster of human blood samples. It was shown by experiments, that the U44-normalized assay can be used to identify the presence of human or higher primate blood if a positive result for an unknown sample was obtained using the U6b-normalized blood assay. Thus, the choice of the right normalizer may provide species specificity.

The method/assay according to the present invention successfully detected the presence of biological material in aged and environmentally compromised samples as well as in simulated casework samples that included admixed body fluid samples, post coital samples and trace body fluid samples and is thus a valuable tool for identifying unknown sample types. As is outlined above, the method/assay of the present application is particularly useful for the determination/identification of forensic samples, and in particular of samples of small quantity. The method/assay can also be used in combination with conventional methods for identifying the nature of a sample, e.g. with methods which detect mRNA targets as markers in order to identify the nature of a sample types.

Also provided is a method for identifying at least one small non-coding RNA as a marker for a particular sample type, comprising at least the following steps:
 a. determining the expression of at least one candidate small non-coding RNA in different sample types;
 b. selecting at least one small non-coding RNA that is differentially expressed in a particular sample type as marker small non-coding RNA for said sample type.

A respective screening/identification method allows the identification of further small non-coding RNAs that can be used as markers for different samples, such as tissue and body fluid samples. The sample can be selected from any human body fluid and tissue samples including but not limited to blood, menstrual blood, semen, saliva, vaginal secretions, skin, brain, lung, testis, adipose, thymus, muscle, spleen, placenta, bone marrow, skin, uterus, salivary gland and liver and other suitable related materials obvious to those skilled in the art. The method is particularly useful for selecting/identifying a marker small non-coding RNA for determining the nature (e.g. origin, tissue type) of a forensic sample. The small non-cording RNA that is detected is preferably a mature miRNA. Suitable candidates are disclosed in FIGS. 1 to 5.

It is advantageous regarding specificity and sensitivity that the small non-coding RNA selected as marker has at least one of the following characteristics:
 a. It is expressed in the particular sample for which the small non-coding RNA serves as marker;
 b. it shows a discriminating/differential expression pattern in a particular type of sample compared to other sample types;
 c. it is specifically expressed in a particular sample type;
 d. it is expressed in higher abundance in a particular sample type; and/or
 e. it is expressed in higher abundance in a particular sample type than the small non-coding RNA used for normalisation and is expressed at lower levels than the small non-coding RNA used for normalisation in other sample types.

In case a Real time PCR is performed, a suitable marker small non-coding RNA can be identified by selecting one which has a significant lower Ct value in a particular sample type.

In order to ensure that the identified small non-coding RNAs are the true source of the obtained expression data, reverse transcription negative (RT–) samples, to which no reverse transcriptase is added, is evaluated. Preferably, no signal is detected in the RT– samples. If a Ct value is, however, obtained for the RT– samples, for these assays, the Ct values should be preferably below the RT– average.

According to one embodiment the method comprises
a. Isolating RNA from the sample
b. optionally quantifying the isolated RNA
c. reverse transcribing the isolated RNA
d. detecting, preferably amplifying at least one marker small non-coding RNA.

Details are described above; we refer to the above disclosure.

Also provided is a kit for determining the nature of a sample, comprising at least one sequence specific oligonucleotide of at least 80% homology, preferably at least 90% complementary to the target sequence for detecting the presence or absence of at least one marker small non-coding RNA in a sequence specific manner. A respective kit allows the easy and routine identification of samples and is particularly useful for forensic applications. The advantages of a respective kit are outlined in detail above. Preferably, the small non-coding RNA that is detected is a mature miRNA.

The kit may comprise oligonucleotides for detecting the presence or absence of at least two marker small-non-coding RNAs in a sample. As is outlined above, the detection of at least two marker small non-coding RNAs increases the reliability of the kit.

Preferably, the marker small non-coding RNA detected by the kit has at least one of the following characteristics:
a. it is expressed in the particular sample for which the small non-coding RNA serves as marker;
b. it shows a discriminating/differential expression pattern in a particular type of sample compared to other sample types;
c. it is specifically expressed in a particular sample type;
d. it is expressed in higher abundance in a particular sample type; and/or
e. it has a significant lower Ct value in a particular sample type; and/or
f. it is expressed in higher abundance in a particular sample type than the small non-coding RNA used for normalisation and is expressed at lower levels than the small non-coding RNA used for normalisation in other sample types.

The advantages are outlined in detail above; we refer to our above disclosure.

The kit may comprise at least one sequence specific oligonucleotide for detecting the presence or absence of at least one marker small non-coding RNA indicative for a sample type selected from the group consisting of blood, menstrual blood, semen, vaginal secret and saliva.

The kit may comprise at least one oligonucleotide specific for at least one small non-coding RNA selected from the group of small non-coding RNAs listed in Table 1 (see FIG. 1), an isoform thereof (having no more than 5, preferably no more than 3 or more preferred no more than 2 base changes) and/or a small non-coding RNA derived from the same premiRNA as the respective small non-coding RNAs listed in Table 1 (see FIG. 1). A respective specific oligonucleotide is preferably at least 80% homologous (identical, respectively complementary) to the respective marker target sequence to allow sequence specific detection.

The respective miRNAs are specifically/differentially expressed in blood samples and in particular peripheral blood and are thus suitable markers for determining/identifying an unknown sample as a blood sample. It is advantageous that at least two small non-coding RNAs are detected which are selected from the following group of small non-coding RNAs as markers for blood:

| |
|---|
| Let7i |
| miR15a |
| miR15b |
| miR16 |
| miR106a |
| miR106b |
| miR126 |
| miR182 |
| miR182* |
| miR185 |
| miR190 |
| miR195 |
| miR374 |
| miR451 |
| miR545 |
| miR624 |
| miR627 |
| miR154* |
| miR607 | or an isoform thereof (having no more than 5, preferably no more than 3 or more preferred no more than 2 base changes) and/or a small non-coding RNA derived from the same premiRNA. Preferably Let7i, miR16, miR451 and/or miR15b, most preferred miR451 and miR16 are detected as marker miRNAs.

It was demonstrated in extensive experiments by the inventors that the respective miRNAs are particularly specific markers for blood which thus allow the secure identification/determination of an unknown sample as a blood sample.

The kit may comprise additionally or alternatively at least one oligonucleotide specific for at least one small non-coding RNA selected from the group of small non-coding RNAs listed in Table 2 (see FIG. 2), preferably miR412 and miR451, or an isoform thereof (having no more than 5, preferably no more than 3 or more preferred no more than 2 base changes) and/or a small non-coding RNA derived from the same premiRNA as the respective small non-coding RNAs listed in Table 2 (see FIG. 2). A respective specific oligonucleotide is preferably at least 80% homologous (identical, respectively complementary) to the respective marker target sequence to allow sequence specific detection. The respective miRNAs are specifically/differentially expressed in menstrual blood samples and are thus suitable markers for determining/identifying an unknown sample as a menstrual blood sample. It is advantageous that at least two small non-coding RNAs are selected from the following group of small non-coding RNAs as markers for menstrual blood:

| |
|---|
| miR23a/b |
| miR33 |
| miR95 |
| miR106b |
| miR154 |
| miR218 |
| miR369-5p |
| miR377 |
| miR412 |
| miR423 |
| miR425-3p |
| miR451 |
| miR452 |
| miR452* |
| miR484 |

| |
|---|
| miR494 |
| miR648 |
| miR369-5p |
| miR507 |
| miR648 | or an isoform thereof (having no more than 5, preferably no more than 3 or more preferred no more than 2 base changes) and/or a small non-coding RNA derived from the same premiRNA. Particularly preferred examples were already described above. It was demonstrated in extensive experiments by the inventors that the respective miRNAs are particularly specific markers for menstrual blood which thus allow the secure identification/determination of an unknown sample as a menstrual blood sample even compared to a peripheral blood sample.

The kit may comprise additionally or alternatively at least one oligonucleotide specific for at least one small non-coding RNA selected from the group of small non-coding RNAs shown in Table 3 (see FIG. 3) or an isoform thereof (having no more than 5, preferably no more than 3 or more preferred no more than 2 base changes) and/or a small non-coding RNA derived from the same premiRNA as the respective small non-coding RNAs listed in Table 3 (see FIG. 3), preferably miR135b and miR10b. A respective specific oligonucleotide is preferably at least 80% homologous (identical, respectively complementary) to the respective marker target sequence to allow sequence specific detection. The respective miRNAs are specifically/differentially expressed in semen samples and are thus suitable markers for determining/identifying an unknown sample as a semen sample. It is advantageous that at least two small non-coding RNAs are selected from the following group of small non-coding RNAs as markers for semen:

| |
|---|
| miR10b |
| miR99a |
| miR135a |
| miR135b |
| miR204 |
| miR508 |
| miR513 |
| miR517a |
| miR518f* |
| miR519d |
| miR520a* |
| miR520g/h |
| miR514 |
| miR518c |
| miR518e |
| miR524* |
| miR611 | or an isoform thereof (having no more than 5, preferably no more than 3 or more preferred no more than 2 base changes) and/or a small non-coding RNA derived from the same premiRNA. It was demonstrated in extensive experiments by the inventors that the respective miRNAs are particularly specific markers for semen which thus allow the secure identification/determination of an unknown sample as a semen sample.

The kit may comprise additionally or alternatively at least one oligonucleotide specific for at least one small non-coding RNA selected from the group of small non-coding RNAs listed in Table 4 (see FIG. 4) or an isoform thereof (having no more than 5, preferably no more than 3 or more preferred no more than 2 base changes) and/or a small non-coding RNA derived from the same premiRNA as the respective small non-coding RNAs listed in Table 4 (see FIG. 4). Preferably miR124a, miR372 and miR195 are detected as marker miRNA. A respective specific oligonucleotide is preferably at least 80% homologous (identical, respectively complementary) to the respective marker target sequence to allow sequence specific detection. Suitable examples for sequence specific oligonucleotides are also indicated in Table 4. The respective miRNAs are specifically/differentially expressed in vaginal secretion samples and are thus suitable markers for determining/identifying an unknown sample as a vaginal secretion sample. It is advantageous that at least two small non-coding RNAs are selected from the following group of small non-coding RNAs as markers for vaginal secretion samples:

| |
|---|
| miR124a |
| miR195 |
| miR372 |
| miR521 |
| miR568 | or an isoform thereof (having no more than 5, preferably no more than 3 or more preferred no more than 2 base changes) and/or a small non-coding RNA derived from the same premiRNA. It was demonstrated in extensive experiments by the inventors that the respective miRNAs are particularly specific markers for vaginal secretions which thus allow the secure identification/determination of an unknown sample as a vaginal secretion sample.

The kit may comprise additionally or alternatively at least one oligonucleotide specific for at least one small non-coding RNA selected from the group of small non-coding RNAs listed in Table 5 (see FIG. 5), preferably miR658 and miR205 or an isoform thereof (having no more than 5, preferably no more than 3 or more preferred no more than 2 base changes) and/or a small non-coding RNA derived from the same premiRNA as the respective small non-coding RNAs listed in Table 5 (see FIG. 5). A respective specific oligonucleotide is preferably at least 80% homologous (identical, respectively complementary) to the respective marker target sequence. Suitable examples for sequence specific oligonucleotides are also indicated in Table 5. The respective miRNAs are specifically/differentially expressed in saliva samples and are thus suitable markers for determining/identifying an unknown sample as a saliva sample. It is advantageous that at least two small non-coding RNAs are selected from the following group of small non-coding RNAs as markers for saliva:

| |
|---|
| miR205 |
| miR206 |
| miR208 |
| miR302c |
| miR509 |
| miR510 |
| miR515-5p |
| miR518c* |
| miR525 |
| miR526b |
| miR551a |
| miR600 |
| miR606 |
| miR555 |
| miR587 |
| miR658 | or an isoform thereof (having no more than 5, preferably no more than 3 or more preferred no more than 2 base changes)

and/or a small non-coding RNA derived from the same premiRNA. It was demonstrated in extensive experiments by the inventors that the respective miRNAs are particularly specific markers for saliva which thus allow the secure identification/determination of an unknown sample as a saliva sample.

Preferably, the kit comprises oligonucleotides for at least two different marker small non-coding RNAs per particular sample type.

Furthermore, the kit may comprise at least one sequence specific oligonucleotide for detecting a small non-coding RNA for normalization. Preferably, the small non-coding RNA detected for normalization has a Ct value close to the Ct value of the marker small non-coding RNA. The kit may comprise at least one sequence specific oligonucleotide for detecting a small non-coding RNA selected from the group consisting of U6B, U44, S15 or miRNAs which have a similar Ct value in all sample types of interest. Details are outlined above, we refer to our above disclosure.

The kit may additionally comprise at least one of the following components
- a. buffers and/or reagents for isolating RNA from a sample
- b. buffers and/or reagents for reverse transcribing RNA
- c. buffers and/or reagents for amplification and/or detection.

Details regarding the isolation, amplification and detection were outlined above; we refer to the respective disclosure. The kit may also comprise a universal oligonucleotide that can be used in combination with the sequence specific oligonucleotide for amplifying the small non-coding RNAs.

A respective kit is particularly useful in for identifying the nature and in particular the origin and type of forensic samples as it provides a reliable tool for determining the nature of even small samples, in particular forensic samples.

Also provided is an oligonucleotide set for determining the nature of a sample, said set comprising oligonucleotides for detecting at least two different small non-coding RNAs per sample type, wherein said oligonucleotide set has at least one of the following characteristics:
- a. It comprises oligonucleotides hybridising to at least two small non-coding RNAs comprising or consisting of a sequence selected from the group of

| miR15a |
| Let7i |
| miR15b |
| miR16 |
| miR106a |
| miR106b |
| miR126 |
| miR182 |
| miR182* |
| miR185 |
| miR190 |
| miR195 |
| miR374 |
| miR451 |
| miR545 |
| miR624 |
| miR627 |
| miR154* |
| miR607 | or hybridising to an isoform thereof (having no more than 5, preferably no more than 3 or more preferred no more than 2 base changes) and/or miRNA derived from the same premiRNA as the respective miRNAs, preferably miR451 and miR16, as markers for blood;

- b. and/or it comprises oligonucleotides hybridising to at least two small non-coding RNAs comprising or consisting of a sequence selected from the group of

| miR23a/b |
| miR33 |
| miR95 |
| miR154 |
| miR218 |
| miR377 |
| miR412 |
| miR423 |
| miR425-3p |
| miR451 |
| miR452 |
| miR452* |
| miR484 |
| miR494 |
| miR648 |
| miR369-5p |
| miR507 |
| miR648 | or hybridising to an isoform thereof (having no more than 5, preferably no more than 3 or more preferred no more than 2 base changes) and/or miRNA derived from the same premiRNA as the respective miRNAs, preferably miR412 and miR451, as markers for menstrual blood;

- c. and/or it comprises oligonucleotides hybridising to at least two small non-coding RNAs comprising or consisting of a sequence selected from the group of

| miR10b |
| miR99a |
| miR135a |
| miR135b |
| miR204 |
| miR508 |
| miR513 |
| miR517a |
| miR518f* |
| miR519d |
| miR520a* |
| miR520g/h |
| miR514 |
| miR518c |
| miR518e |
| miR524* |
| miR611 | or hybridising to an isoform thereof (having no more than 5, preferably no more than 3 or more preferred no more than 2 base changes) and/or miRNA derived from the same premiRNA as the respective miRNAs, preferably miR135b and miR10b, as markers for semen;

- d. and/or at it comprises oligonucleotides hybridising to at least two small non-coding RNAs comprising or consisting of a sequence selected from the group of

| miR124a |
| miR195 |
| miR372 |
| miR521 |
| miR568 | or hybridising to an isoform thereof (having no more than 5, preferably no more than 3 or more preferred no more than 2 base changes) and/or miRNA derived from the same premiRNA as the respective miRNAs, preferably miR124a, miR372 and miR195, as markers for vaginal secretions;

e. and/or it comprises oligonucleotides hybridising to at least two small non-coding RNAs comprising or consisting of a sequence selected from the group of

| |
|---|
| miR205 |
| miR206 |
| miR208 |
| miR302c |
| miR509 |
| miR510 |
| miR515-5p |
| miR518c* |
| miR525 |
| miR526b |
| miR551a |
| miR600 |
| miR606 |
| miR555 |
| miR587 |
| miR658 | or hybridising to an isoform thereof (having no more than 5, preferably no more than 3 or more preferred no more than 2 base changes) and/or miRNA derived from the same premiRNA as the respective miRNAs, preferably miR658 and miR205, as markers for saliva.

A respective oligonucleotide set is particularly useful for identifying/typing samples, in particular body fluids. The features of the respective small non-coding RNAs are described in detail above. Each oligonucleotide hybridises to its specific/corresponding marker small non coding RNA. Hence, if the set comprises oligonucleotides hybridising to at least two small non-coding RNAs, at least two different oligonucleotides are provided wherein each oligonucleotide recognises a specific marker small non coding RNA. The oligonucleotides do not need to recognise both sequences even though this option is included. Some small non coding RNAs exist with minor sequence variations (e.g. miRNA isoforms having less than 5, preferably 2 or 3 base changes or less). They are also encompassed as the individual oligonucleotides can be designed that they also recognize and hybridise to respective miRNA isoforms or miRNAs which are derived from the same premiRNA.

FIG. 1-5 show tables 1-5 which depict suitable miRNAs which are useful markers for different samples, namely blood (FIG. 1/Table 1), menstrual blood (FIG. 2/Table 2), semen (FIG. 3/Table 3), vaginal secretions (FIG. 4/Table 4) and saliva (FIG. 5/Table 5).

Figure 9:
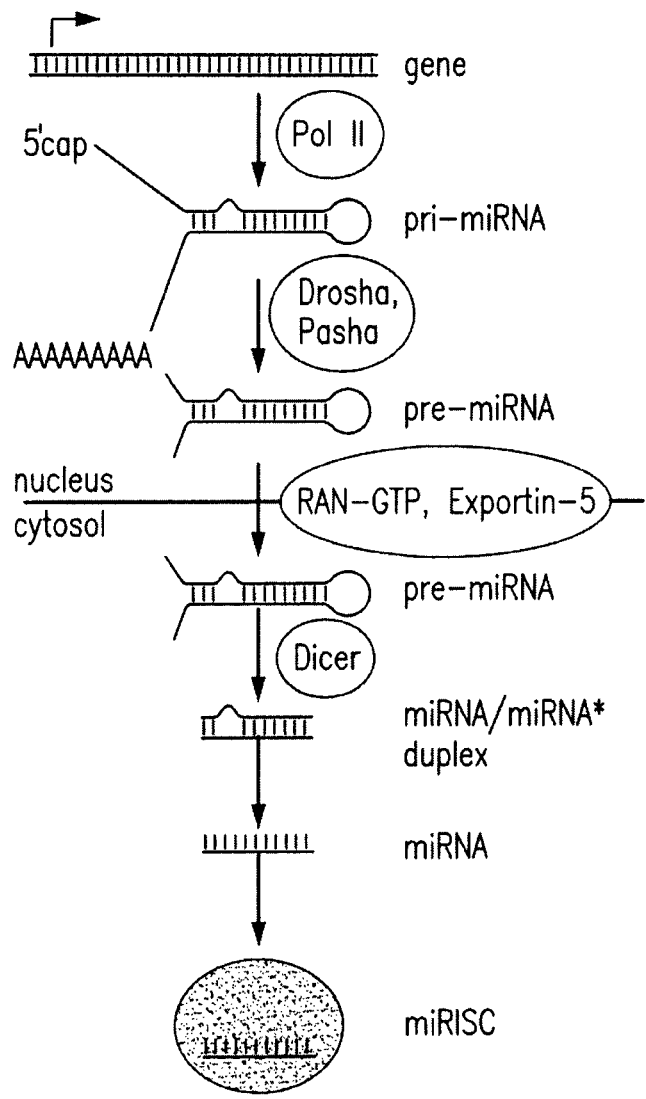
FIG. 9 shows the generation of mature miRNAs according to one assumed embodiment.

As is also shown in FIG. 9, a mature miRNA is made from a stem loop precursor, typically from one leg of the stem. When the other leg is detected as a minor component in the cells, it gets the asterisk. When both strands are detected as relatively equal contributors, they get 3p and 5p suffix (depending on whether they are closer to the 5' or 3' end of the premiRNA). Some miRNA have an identical mature sequence but different names. This naming schema corresponds to the one of miRBase. If several isoforms of a miRNA exist that can be detected, respective isoforms (having suffices a, b, c etc). Isoforms differ in only a few bases, usually less than 3. Further isoforms may exist, which are not listed but could also be detected according to the teachings of the present invention. "hsa" is the designation for human miRNA sequence. Particularly preferred variants/isoforms are indicated in the tables.

FIG. 6 shows, as an example, the results of a miRNA candidate screening using pooled body fluid samples. The graph shows absolute Ct values for 25 miRNAs for the pooled body fluid samples for identification of possible miRNA marker candidates for the individual body fluids, namely blood, semen, saliva, vaginal secretions and menstrual blood.

Each body fluid is represented by a symbol (blood—diamond; semen—small square; saliva—triangle; vaginal secretions—large square; menstrual blood—circle).

As can be seen, only few miRNAs depict an expression profile which makes them suitable as marker small non-coding RNAs according to the present invention. For example, the graph shows that the miRNAs miR15a, miR15b and miR16 are suitable candidates for blood samples as they show a desirable discrimination profile compared to the other body fluids analysed. They can thus be used as a marker for blood.

FIG. 7A to E shows the development of 2-D miRNA body fluid identification assays. Different samples from different donors were used. Body fluid data clustering using 2-D scatter plots constructed with U6b normalised expression data for two miRNAs that were particularly advantageous markers for the respective fluid is shown. The blood assay (FIG. 7A) shows in the X-axis the ΔCt miR16 (U6b-miR16), the Y-axis the ΔCt miR451 (U6b-miR451). The semen assay (FIG. 7B) shows on the X-axis the ΔCt of miR135b (U6b-miR135b), the Y-axis shows the ΔCt of miR10b (U6b-miR10b). The saliva assay (FIG. 7C) shows on the X-axis the ΔCt of miR205 (U6b-miR205) and on the Y-axis the Δ-Ct of miR658 (U6b-miR658). The vaginal secretion assay (FIG. 7D) shows on the X-axis the ΔCt of miR124a (U6b-miR124a) and on the Y-axis the ΔCT of miR372 (U6b-miR372). The menstrual blood assay (FIG. 7E) shows on the X-axis ΔCt miR451 (U6b-miR451), the Y-axis shows the ΔCt miR412 (U6b-miR412).

The body fluids are presented by symbols. The blood is represented by squares, the semen by diamonds, saliva by triangles, vaginal secretions by a circle and menstrual blood by open squares. The body fluid of interest on each assay is circled and labelled.

A pair of markers was used, as the use of two markers provides more security for identifying/typing a specific sample. As can be seen, the tested markers are plotted in the shown 2-D assay in the same quadrant which indicates that they are equally suitable. Furthermore, as can be seen from the results obtained from the different samples, the tested markers are also highly specific for their respective sample type.

Figure 8:
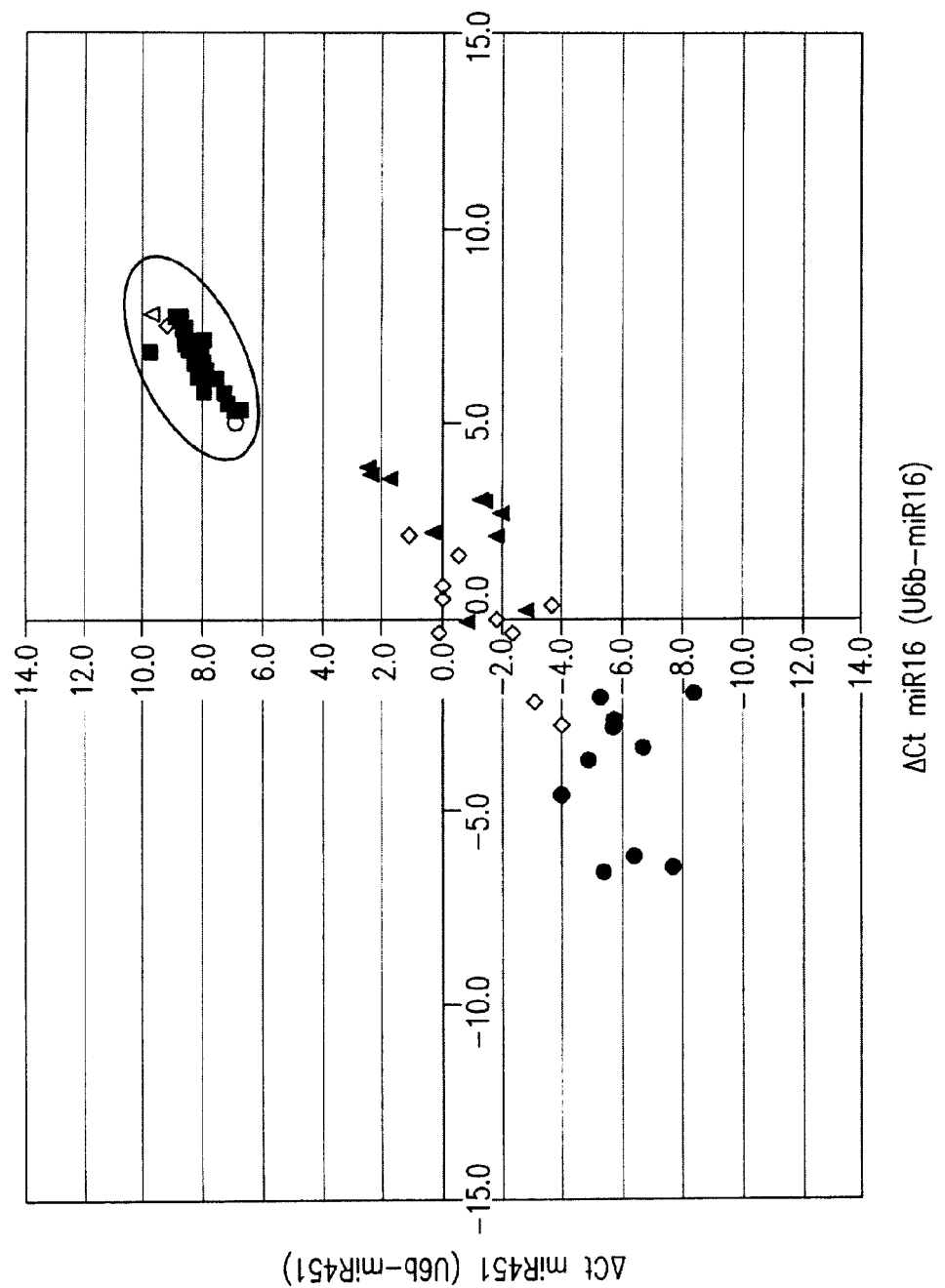
FIG. 8 shows the stability of miRNA expression even in environmentally compromised.

FIG. 8 demonstrates the stability of miRNA expression even in environmentally compromised blood samples.

FIG. 9 illustrates the generation of mature miRNAs according to one assumed embodiment (figure obtained from public sources). The genes encoding miRNAs are much longer than the processed mature miRNA molecule. miRNAs are first transcribed as primary transcripts or pri-miRNA with a cap and poly-A tail and processed to short, approximately 70-nucleotide stem-loop structures known as pre-miRNA in the cell nucleus. This processing is performed in animals by a protein complex known as the Microprocessor complex, consisting of the nuclease Drosha and the double-stranded RNA binding protein Pasha. These pre-miRNAs are then processed to mature miRNAs in the cytoplasm by interaction with the endonuclease Dicer, which also initiates the formation of the RNA-induced silencing complex (RISC). This complex is responsible for the gene silencing observed due to miRNA expression and RNA interference. The pathway is also different for miRNAs derived from intronic stem-loops; these are processed by Dicer but not by Drosha. Either the sense strand or antisense strand of DNA can function as templates to give rise to miRNA. Most pre-miRNAs don't have a perfect double-stranded RNA (dsRNA) structure topped by a terminal loop. There are few possible explanations for such selectivity. One could be that dsRNAs longer than 21 base pairs activate interferon response and anti-viral machinery in the cell. Another plausible explanation could be that the thermodynamic profile of pre-miRNA determines which strand will be incorporated into Dicer complex. Indeed, clear similarities between pri-miRNAs encoded in respective (5'- or 3'-) strands have been demonstrated. When Dicer cleaves the pre-miRNA stem-loop, two complementary short RNA molecules are formed, but only one is integrated into the RISC complex. This strand is known as the guide strand and is selected by the argonaute protein, the catalytically active RNase in the RISC complex, on the basis of the stability of the 5' end. The remaining strand, known as the anti-guide or passenger strand, is degraded as a RISC complex substrate. After integration into the active RISC complex, miRNAs base pair with their complementary mRNA molecules and induce mRNA degradation by argonaute proteins, the catalytically active members of the RISC complex.

EXAMPLES

For identifying useful marker small non-coding RNAs and in particular miRNAs, the commercially available "Human miScript Oligonucleotide Assay Set V1.0—miRNA-specific oligonucleotides for 452 human miRNAs"; QIAGEN cat no 218411 can be used to screen for markers useful in forensic testing. Suitable candidates are listed in FIG. 1 to 5.

Example 1

Tissue Identification 4 different sample types are collected from 5 different individuals of different sex (if applicable) and age: semen, blood, saliva, vaginal secretion. RNA is extracted from these samples and RNA pools are generated from RNA from all 5 donors. RNA is quantified and subjected to real time PCR based analysis to determine expression levels for the individual miRNAs respectively. Candidate miRNAs are identified that show significantly heightened or lowered expression levels for certain samples, e.g. body fluids.

Example 2

Stability

Different sample types (semen, blood, saliva, vaginal secretion) are collected, stored at room temperature and total RNA is extracted at different time points from 0 to 18 months. miRNAs are found to be highly stable.

The ability to detect the body fluids in environmentally compromised biological stains was evaluated by the analysis of samples stored at room temperature (one year and two years) and at 37° for six months. The blood assay was performed as described above. The markers miR16 and MiR451 were used for detection. The X-axis indicates the ΔCt of miR16, the Y-axis the ΔCt of miR451.

Several body fluids and the compromised samples were tested. Blood is indicated by squares, semen by diamonds, saliva by triangles and vaginal secretions by circles. The known blood samples (see above) are circled in the graph. The room temperature one year sample is represented by an open triangle in the blood section, the room temperature two year sample is represented by an open square and the 37° six months sample is represented by an open diamond. As can be seen, the results are basically identical for all samples despite the fact that the additionally tested blood samples were aged/heat treated. The results demonstrate, that for example, blood stains kept at room temperature for even two years and even at elevated temperatures still cluster as blood stains and can thus be securely identified by detecting the marker miRNAs. This proves that the present detection method is highly reliable also for difficult and/or compromised samples, which are often encountered in forensic samples. The marker miRNA are stable in the sample and thus provide a reliable marker that can be detected to identify/type samples. Additional test were performed.

Example 3

Additional Experiments

To further substantiate the respective results, additional experiments were performed.
3.1. Methods
a.) Preparation of Body Fluid Stains Body fluids were collected from volunteers using procedures approved by the University of Central Florida's Institutional Review Board. Informed written consent was obtained from each donor. Blood samples were collected by venipuncture into additive-free vacutainers and 50 μl aliquots were placed onto cotton cloth and dried at room temperature. Freshly ejaculated semen was provided in sealed plastic tubes and stored frozen until they were dried onto sterile cotton swabs. Saliva samples were provided in sealed plastic tubes and stored frozen until they were dried onto sterile cotton swabs. Buccal samples were collected from donors using sterile swabs by swabbing the inside of the donor's mouth. Semen-free vaginal secretions and menstrual blood were collected using sterile cotton swabs. All samples were stored at −20° C. until needed. A 50 μl stain or a single cotton swab was used for RNA isolation.

Total RNA from 20 human tissues (adipose, bladder, brain, cervix, colon, esophagus, heart, kidney, liver, lung, ovary, placenta, prostate, skeletal muscle, small intestine, spleen, testes, thymus, thyroid, and trachea) included in the FirstChoice® Human Total RNA Survey Panel was obtained from Applied Biosystems/Ambion (Austin, Tex.). All tissues included in the panel were 3-donor pooled samples and were certified to contain small RNAs including miRNAs and snRNAs. Total RNA from human skin was obtained from Biochain Institute, Inc (Hayward, Calif.).

Blood samples from 12 non-primate animal species (dog, cat, horse, crane, cow, sheep, coyote, tortoise, lamb, Patagonian cavy, ferret, deer) and 10 primate species (spider monkey, rhesus macaque, pig-tailed macaque, brown lemur, chimpanzee, baboon, howler monkey, cynomolgous monkey, African green monkey, and spot-nosed guenon) were obtained from various sources: Tuscawilla Oaks Animal Hospital, Oviedo, Fla. (dog, cat); HemoStat Laboratories, Dixen, Calif. (sheep, cow, horse); Central Florida Zoo, Sanford, Fla. (brown lemur, howler monkey, spot-nosed guenon); Brevard Zoo, Melbourne, Fla. (crane, coyote, tortoise, lamb, Patagonian cavy, spider monkey, rhesus macaque, pig-tailed macaque); donation from laboratory members (coyote, deer); West End Animal Hospital, Gainesville, Fla. (ferret). Liquid blood samples from African green monkey, cynomolgus monkey, baboon and chimpanzee were obtained from Bioreclamation, Inc. (Westbury, N.Y.). For all blood samples, fifty microliter aliquots were placed on cotton cloth and dried overnight at room temperature.

Saliva samples from two cats and two dogs were collected by swabbing the inside of the animal's mouth using sterile cotton swabs. A primate saliva sample (spot-nosed guenon) was obtained by donation from the Central Florida Zoo (Sanford, Fla.).

b) RNA Isolation

Total RNA was extracted from blood, semen, saliva, vaginal secretions and menstrual blood with guanidine isothiocyanate-phenol:chloroform and precipitated with isopropanol [58]. Briefly, 500 □l of pre-heated (56° C. for 10 minutes) denaturing solution (4M guanidine isothiocyanate, 0.02M sodium citrate, 0.5% sarkosyl, 0.1M beta-mercaptoethanol) was added to a 1.5 mL Safe Lock tube extraction tube (Eppendorf, Westbury, N.Y.) containing the stain or swab. The samples were incubated at 56° C. for 30 minutes. The swab or stain pieces were then placed into a DNA IQ™ spin basket (Promega, Madison, Wis.), re-inserted back into the original extraction tube, and centrifuged at 14,000 rpm (16,000×g) for 5 minutes. After centrifugation, the basket with swab/stain pieces was discarded. To each extract the following was added: 50 µl 2 M sodium acetate and 600 µl acid phenol:chloroform (5:1), pH 4.5 (Applied Biosystems/Ambion). The samples were placed at 4° C. for 30 minutes to separate the layers and then centrifuged for 20 minutes at 14,000 rpm (16,000×g). The RNA-containing top aqueous layer was transferred to a new 1.5 ml microcentrifuge tube, to which 2 µl of GlycoBlue™ glycogen carrier (Applied Biosystems/Ambion) and 500 µl of isopropanol were added. RNA was precipitated for 1 hour at −20° C. The extracts were then centrifuged at 14,000 rpm (16,000×g). The supernatant was removed and the pellet was washed with 900 µl of 75% ethanol/25% DEPC-treated water. Following a centrifugation for 10 minutes at 14,000 rpm (16,000×g), the supernatant was removed and the pellet dried using vacuum centrifugation (56° C.) for 3 minutes. Twenty microliters of pre-heated (60° C. for 5 minutes) RNAsecure™ solution (Applied Biosystems/Ambion) was added to each sample followed by an incubation at 60° C. for 10 minutes. Samples were used immediately or stored at −20° C. until needed.

c) DNase I Digestion

Six units of TURBO™ DNase I (2U/µl) (Applied Biosystems/Ambion, Inc.) and 2.2 µl of Turbo DNase I Buffer (10×) were added to each RNA extract and incubated at 37° C. for 1 hour. The DNase was inactivated at 75° C. for 10 minutes. The samples were used immediately or stored at −20° C. until needed. Alternatively, DNase digestion was performed using the Turbo DNA-free™ kit (Applied Biosystems/Ambion) according to the manufacturer's protocol.

d) RNA Quantitation

RNA extracts were quantitated with Quant-iT™ RiboGreen® RNA Kit (Invitrogen, Carlsbad, Calif.). Fluorescence was determined using a Synergy™ 2 Multi-Mode microplate reader (BioTek Instruments, Inc., Winooski, Vt.).

e) cDNA Synthesis

For the reverse transcriptase (RT) reaction, the miScript Reverse Transcription Kit (Qiagen, Valencia, Calif.) was used according to manufacturer's protocols. One nanogram of total RNA from blood, semen, vaginal secretions and menstrual blood extracts and 5 ng of total RNA from semen extracts were used in the RT reactions. A reverse transcription negative reaction (containing total RNA and reaction buffer but no reverse transcriptase enzyme mix) was performed for each sample.

f) Real-Time Polymerase Chain Reaction

Real-time PCR was performed using the Relative Quantitation protocol on an ABI Prism 7000 Sequence Detection System (Applied Biosystems). One microliter of the 1 ng RT-reaction (blood, saliva, vaginal secretions, menstrual blood) and two microliters of the 5 ng RT-reaction (semen) were amplified using the miScript SYBR® Green PCR kit and a 10× miScript primer assay (Human miScript Primer Assay Set v1.0, Qiagen) according to manufacturer's protocols, with minor modifications. A reduced reaction volume of 25 µl was used as well as an increased number of amplification cycles (from 35-40 to 50 cycles). Additional snRNA (U6b) and snoRNA (U26, U27, U28, U29, U30, U31, U38B, U43, U44, U48 and U90) primer assays for normalization studies were obtained from Qiagen.

g) Menstruation Cycle Samples

Two female individuals donated vaginal swabs over the course of a 28-day period. Females at two different life stages participated in the study, one experiencing menstruation at regular intervals and one in perimenopause. Participants were asked to collect a single semen-free vaginal swab during each day of the study, with the first day of collection starting on the first day of menstruation if applicable.

h) Multiple-Source Samples

Pooled Samples

Five-donor pooled samples were used for the initial miRNA screening in forensically relevant fluids. Total RNA from each individual sample was extracted and quantitated as described above. Equal quantities of total RNA from each donor were combined in order to produce a 1 ng/□l pooled sample for blood, saliva, vaginal secretions and menstrual blood, and a 5 ng/µl pooled sample for semen. A 1 µl aliquot of each pooled sample was used in the reverse transcription assay.

Two Fluid Mixtures

Admixed body fluid samples (blood-semen, blood-saliva, blood-vaginal secretions, semen-saliva, semen-vaginal secretions and saliva-vaginal secretions) were created by combining two different body fluid stains or swabs (50 µl stain for blood, semen and saliva, or a single vaginal secretion swab) in the same tube. Total RNA was extracted as described above.

i) Mock Casework Samples

Saliva Samples

Swabs of a beverage container lid (plastic coffee cup lid, water bottle) using a sterile cotton swab were collected after being deposited by volunteers. Saliva from a male donor was deposited onto the skin of a female donor. After the saliva was allowed to dry, the skin was swabbed using a sterile cotton swab. Portions of the outer wrapping of used cigarette butts (collected from a male and female donor) were removed for extraction. Total RNA was extracted as described above.

3.2. Results 3.2.1. miRNA BodyFluID Specificity a) Body Fluid/Tissue Specificity The initial studies were performed using five samples per body fluid (se above). In order to ensure the specificity of each assay, additional body fluid samples were tested (n=10-20 for the body fluid of interest, n=8-10 for the other body fluids not being assayed for).

Blood

Nineteen human blood samples (including the five previously tested samples) were analyzed using the blood miRNA assay (miR16/deltaCt miR451). The blood sample donors, both male and female, ranged in age from 15 months to 84 years old. As before, all of the human blood samples were found in a distinct cluster in the upper right quadrant separated from all other body fluids. All vaginal secretion samples were found in the lower left quadrant and there was considerable overlap of the semen and saliva samples, which were spread out over the two lower quadrants and the upper right quadrant. The buccal samples were located closer to the blood samples than any of the other fluids but were still well separated from each other.

Semen

Eleven human semen samples (five previously tested samples included) were tested using the semen miRNA assay (deltaCt miR135b and deltaCt miR10b). Samples were obtained from adult males ranging in age from 26-52 years old. All of the semen samples are found in a distinct cluster separated from all other body fluids. Samples from two vasectomized males were included in the study in order to determine if the semen assay was specific to sperm cells. Both of the samples from the vasectomized males were detected amongst the semen samples from non-vasectomized males, thereby demonstrating the ability of the assay to accommodate non-sperm containing semen samples. The detection of semen from both vasectomized and non-vasectomized males could indicate that the two semen miRNA candidates are present in seminal fluid or in epithelial cells from the male reproductive tract. Overall, fewer miRNAs were detected in semen compared to the other biological fluids and those that were present were often found in much lower abundance. The low abundance of these miRNAs may be explained if detection is obtained from the low level of non-sperm cells present in semen. The cellular and non-cellular components of semen could be separated and examined for the presence of both of the semen miRNA candidates to determine if the miRNAs used in the semen assay are cellular based.

Saliva

Eighteen human saliva samples (including the five previously tested samples) were tested using the saliva miRNA assay (miR205/miR658). Samples were obtained from both male and female donors ranging in age from 26-58 years old, and included both liquid whole saliva samples (n=9) and buccal swabs (n=9). All of the liquid saliva and buccal scrapings samples were located together in a distinct cluster separate from the other body fluids tested. They were clustered in the upper right quadrant with the exception of one buccal sample which, although part of the cluster, was slightly outside the quadrant. The vaginal secretions, blood and semen samples were mainly located in the lower left quadrant with a few samples just inside the lower right quadrant. The ability to identify both liquid saliva and buccal samples is an important finding since both whole saliva and buccal cells are encountered in forensic specimens.

Vaginal Secretions

Eleven vaginal secretion samples (including the five previously analyzed samples) were collected from adult females ranging in age from 28-65 years old and tested using the vaginal secretions miRNA assay (miR124a/deltaCt miR372). All vaginal secretion samples, except for one 'false negative', were located together in a distinct cluster in the lower right quadrant separate from the other body fluids. Since the whole saliva sample set was the closest to the vaginal cluster, additional saliva samples comprising five buccal epithelial samples were tested using the vaginal secretions assay in order to determine whether the vaginal epithelial and oral epithelial cells were distinguishable. While the buccal epithelial cells clustered closer to the vaginal secretion data points than the whole saliva samples, there was still a clear separation between the two body fluids.

Other Human Tissues

Despite reports in the current literature of the identification of tissue-specific miRNAs, it has been suggested that a majority of miRNAs will be expressed in the majority of tissues. While all of the miRNAs included in the body fluid identification panel described above were detected in each body fluid, their differential expression enabled each of the four body fluids to be distinguished.

Total RNA from twenty-one human tissues including adipose, brain, cervix, heart, liver, lung, placenta, prostate, skeletal muscle, testes, thyroid, trachea, bladder, spleen, thymus, ovary, kidney, colon, esophagus, small intestine (FirstChoice® Human Total RNA Survey Panel, Applied Biosystems/Ambion) and skin (Biochain Institute, Inc.), was analyzed using the miRNA panel. Each total RNA sample included in the FirstChoice® panel comprised RNA from at least three different donors and was certified to contain small RNAs (miRNA, siRNA and snRNA). As expected, the miRNAs included in the panel were detected in each of the tissue samples but again in varying abundance. The high degree of specificity of each of the miRNA body fluid identification assays was confirmed since all of the tissue samples exhibited expression profiles that differed from that of the appropriate body fluid in each of the four assays discussed above.

For the blood assay, both miR16 and miR451 were detected in all twenty-one tissues with the exception of the small intestine where miR451 was not detected. MiR451 was found in the highest abundance in lung and placenta whereas miR16 was found in the highest abundance in lung and prostate. However, despite their higher abundance in these tissues compared to the rest of the samples, their abundance was still lower than that in human blood samples. When the tissue samples were evaluated using blood assay and the data analyzed using the 2D scatter plot, all of the tissue samples were present in the lower left quadrant of the scatter plot whereas the blood samples were tightly clustered in the upper right quadrant.

Both the semen markers, miR135b and miR10b, were also detected in all of the twenty-one tissues with many present in moderate to high abundance. MiR135b was detected in highest abundance in testes and thyroid, whereas miR10b was detected in high abundance in numerous tissues including testes, adipose, cervix, ovary, kidney and colon. As a result of the high abundance of these miRNAs in numerous tissues, the separation between the human semen sample cluster and the tissue samples was not as great in the 2D scatter plot as that observed for the blood assay.

One of the saliva miRNA markers, miR658, was present in low abundance in all of the tissue samples. MiR205 was present in moderate abundance in the cervix, placenta and prostate tissue but in low abundance in all other tissues. The 2D plot showed the tissue samples located in the lower left quadrant with a significant separation from the saliva samples, which were located in the upper right quadrant.

For the vaginal secretions assay all tissue samples were located in the lower left quadrant separated from the vaginal secretions samples that were located in the lower right quadrant. Several published studies have identified miR124a as a brain-specific miRNA. While miR124a was found in highest abundance in brain compared to the other tissues examined, the expression level observed in brain was still lower than that we observed for vaginal secretions. Due to these differences in expression, the brain sample was located closer to the vaginal secretions samples on the two-dimensional plot but was still present in the lower left quadrant. The Ct values for miR372 ranged from 32 to >40 for all tissue samples, with the lowest Ct value obtained from placenta.

Species Specificity

Optimal forensic analysis not only requires an assay to possess tissue specificity but it also should exhibit restricted species specificity. To check this, a number of non-human blood samples were analyzed including twelve animal species (dog, cat, horse, crane, cow, coyote, sheep, tortoise, lamb, Patagonian cavy, ferret, deer) and ten non-human primate species (spider monkey, rhesus macaque, pig-tailed macaque, brown lemur, chimpanzee, baboon, howler monkey, cynomolgus monkey, African green monkey, spot-nosed guenon). A smaller number of non-human saliva samples were available tested and included cat, dog and one primate (spot-nosed guenon). Semen and vaginal secretion samples from non-human species were not available for testing, but such body fluids from non-human species are rarely encountered in casework.

For all of the non-human species blood samples, miR451, miR16, and U6b were detected in significant abundance. All of the non-human samples were found in close proximity to the human blood data points. Two animals (ferret and coyote) and four primates (chimpanzee, baboon, African green monkey, and cynomolgus monkey) were located directly within the human blood cluster. While only a small number of the species tested were clustered within the human blood samples, the small distance between the human data points and the remaining animal species would make it difficult to differentiate human and non-human blood samples with any degree of confidence using this assay.

Saliva samples from two dogs and two cats were used to examine the species specificity of the saliva miRNA assay. Negative results (i.e. not found in the human saliva data cluster) were obtained for the both of the cat and dog samples. While an extensive number of animal saliva samples were not available for testing, cat and dog represent animals that could be frequently encountered at crime scenes in forensic casework.

As a result of the observed species specificity of the blood assay, an improvement was developed in order to provide a more forensically relevant assay. Attempts were made to identify an alternative small RNA to be used for normalization of the miRNA expression data that would also allow for a differentiation of human and non-human blood stains. The expression of 11 small nucleolar RNAs (snoRNAs), including U26, U27, U28, U29, U30, U31, U38B, U43, U44, U48 and U90, was examined in both human and non-human blood samples in order to determine if a human specific normalizer could be identified. Several of the snoRNAs, including U26, U28, U30, U44, and U90, were found in very low abundance or were not detected in the non-human samples. However, the abundance of these snoRNAs in the some of the human body fluids was also quite low. For example, the Ct value for U44, U26, U28, and U90 in semen was over 40 whereas the Ct for U30 was acceptable for semen but was close to 40 for blood and saliva. Therefore, none of the snoRNAs tested were determined to be suitable for use a universal normalizer for all body fluids.

While an alternative universal normalizer was not identified, several of the snoRNAs, including U26, U28 and U44, were present in low abundance in non-human blood samples and in higher abundance in human blood samples. Therefore, it was possible that one of these snoRNAs could be used to normalize only the blood assay and provide the desired species specificity. U44 was selected as the top snoRNA candidate due to its high abundance in blood, its low abundance in the animal blood samples, but also because of its low abundance or absence in most of the primate samples. When the 2D scatter plot was constructed using the U44-normalized data, the clustering that was achieved with the U6b-normalized assay was not achieved and overlap of the semen, saliva and blood data was observed. However, it was evident from the 2D scatter plot that there was a clear separation between the human blood data points and the non-human blood samples. Based on these results, it was determined that the U44-normalized assay could be used to identify the presence of human or higher primate blood if a positive result for an unknown sample was obtained using the U6b-normalized blood assay.

b) Simulated Forensic Casework Samples

The initial studies described above demonstrated the sensitivity (50 pg of input cDNA), specificity (no cross-reactivity with human tissues) and stability (detection in environmentally compromised samples) of the developed miRNA assays for body fluid identification. However, forensic evidentiary items may contain only trace amounts of genetic material and may also include the presence of multiple different biological fluids. Thus it is important to test the performance of the miRNA BodyFluID assays according to the present invention with such samples and we accomplished this by the preparation and analysis of simulated casework samples.

Saliva

Genetic profiles can be routinely recovered from trace amounts of salivary fluids from items such as used cigarette butts and beverage containers. Therefore if the presence of trace amounts of saliva could be detected on these items, it may provide investigators with an indication of which evidentiary items may be useful for the subsequent recovery of DNA. Furthermore, saliva recovered from the skin of a victim could be useful in the investigation of oral assault cases. In order to determine if the saliva miRNA assay could detect trace amounts of saliva in such samples, total RNA was recovered from swabs of beverage container lids, human skin on which saliva had been deposited, and used cigarette butts. All of the simulated casework samples, except for one of the swabs taken from a beverage container lid, were located clustered with the known human saliva samples in the upper right quadrant.

Blood

Total RNA was recovered from the cotton pad of an adhesive bandage used to cover a small cut on the finger of a female donor. The cotton pad of the bandage contained blood in the form of a small reddish-brown stain. When the bandage sample was evaluated with the blood assay, the sample data was located in the upper right quadrant on the two-dimensional scatter plot clustered with the known blood samples. The same sample was subsequently evaluated with the U44-normalized blood miRNA assay in order to determine if the blood present on the bandage was of human origin. The location of the sample on the two-dimensional U44-normalized scatter plot was upper right quadrant clustered with the known human blood samples confirming the presence of human blood present on the bandage.

Semen and Vaginal Secretions

A significant number of samples processed in an operational forensic DNA laboratory involve the analysis of evidence recovered from sexual assaults. Often only a small amount of semen from the perpetrator will be present amongst a vast excess of a female victim's biological material. For an assay to be useful in forensic casework, it must be able to detect the small amount of semen that may be present and not be masked by the excess vaginal material present. In order to determine the potential utility of the semen miRNA assay for the analysis of sexual assault evidence, a vaginal and cervicovaginal swab was collected from a female donor 18 hours post-coitus. The vaginal and cervicovaginal swabs were collected in order to determine if semen would be detected in different regions of the vaginal canal. To insure that residual semen from prior sexual relations were not present, a pre-coital cervicovaginal swab was also obtained before coitus commenced but after an abstinence period of seven days. The presence of semen was detected on both the vaginal and cervicovaginal swabs taken 18 hours post-coitus. The pre-coital swab was negative for the presence of semen. The presence of vaginal secretions was detected in the vaginal swab, cervicovaginal swab and the pre-swab using the vaginal secretions assay.

Body Fluid Mixtures

Body fluid mixtures other than the common semen-vaginal secretions encountered in sexual assault cases may also be present in forensic evidentiary samples. Thus additional body fluid mixtures samples, including two blood-semen and one semen-saliva mixtures were also evaluated. The miRNA expression profile for each mixture using all four body fluid assays (blood, semen, saliva, and vaginal secretions) was determined. Blood and semen were correctly identified in both of the blood-semen mixture samples. On the blood assay, the admixed samples were located in the upper right quadrant clustered with the known blood samples. On the semen assay, the samples were located in the upper portion of the lower right quadrant clustered with the known semen samples. The absence of saliva and vaginal secretions was also demonstrated with the blood-semen mixture samples located in the lower left quadrants. Semen and saliva were also correctly identified in the semen-saliva mixture sample with the sample clustered with the known samples on each plot. The absence of blood and vaginal secretions was also demonstrated.

The examples demonstrate that miRNAs are present in total RNA isolates from body fluid stains in sufficient quantity for analysis. A preferred panel of 9 differentially expressed miRNAs for the identification of the body fluid origin of biological stains was tested using suitable oligonucleotides in detail as described above. The following marker miRNAs are included in said panel: miR451 and miR16 for the identification of blood, miR135b and miR10b for the identification of semen, miR658 and miR205 for the identification of saliva, miR124a and miR372 for the identification of vaginal secretions, and miR412 which is used in combination with the blood candidate miR451 for the identification of menstrual blood. The normalized expression of each of the miRNA pairs exhibits a body fluid-specific expression pattern which allows for an identification of the body fluid of interest.

The respective miRNA assays successfully detected the presence of biological material in aged and environmentally compromised samples as well as in simulated casework samples that included admixed body fluid samples, post coital samples and trace body fluid samples. Additional miRNA candidates for use in the body fluid identification assays can be identified using the methods described herein.

The invention claimed is:

1. A method for determining the type of a forensic sample, comprising:
   a. obtaining RNA from the forensic sample; and
   b. analyzing expression of at least two marker miRNAs, or isoforms thereof, in the forensic sample,
   wherein based on the expression of the miRNAs, or isoforms thereof, the type of forensic sample is determined to be blood, menstrual blood, semen, vaginal secretion or saliva
   and wherein determining the sample is blood comprises analyzing expression of at least two miRNAs listed in Table 1, determining the sample is menstrual blood comprises analyzing expression of at least two miRNAs listed in Table 2, determining the sample is semen comprises analyzing expression of at least two miRNAs listed in Table 3, determining the sample is vaginal secretion comprises analyzing expression of at least two miRNAs listed in Table 4, and determining the sample is saliva comprises analyzing expression of at least two miRNAs listed in Table 5.

2. The method according to claim 1, comprising analyzing at least three marker miRNAs.

3. The method according to claim 1, wherein
   a. the miRNAs, or isoforms thereof, are expressed in the forensic sample and serve as a marker;
   b. the miRNAs, or isoforms thereof, show a discriminating/differential expression pattern in a particular type of forensic sample compared to other types of forensic samples;
   c. the miRNAs, or isoforms thereof, are specifically expressed in a particular type of forensic sample; and/or
   d. the miRNAs, or isoforms thereof, are expressed in higher abundance in a particular type of forensic sample.

4. The method according to claim 1, wherein at least two marker miRNAs, or isoforms thereof, are detected as markers for one particular forensic sample type, and/or wherein at least two marker miRNAs, or isoforms thereof, specific for each different forensic sample type are analyzed in parallel in order to identify the type of forensic sample.

5. The method according to claim 1, wherein
   a. the at least two miRNAs, or isoforms thereof, for determining blood are selected from the group consisting of miR15a, Let7i, miR15b, miR16, miR106a, miR106b, miR126, miR182, miR182*, miR185, miR190, miR195, miR374, miR451, miR545, miR624, miR627, miR154*, and miR607;
   b. the at least two miRNAs, or isoforms thereof, for determining menstrual blood are selected from the group consisting of miR33, miR23a/b, miR95, miR106b, miR154, miR218, miR377, miR412, miR423, miR425-3p, miR451, miR452, miR452*, miR484, miR494, miR648, miR369-5p, miR507, and miR648;
   c. the at least two miRNAs, or isoforms thereof, for determining semen are selected from the group consisting of miR10b, miR99a, miR135a, miR135b, miR204, miR508, miR513, miR517a, miR518f*, miR519d, miR520a*, miR520g/h, miR514, miR518c, miR518e, miR524*, and miR611;
   d. the at least two miRNAs, or isoforms thereof, for determining vaginal secretion are selected from the group consisting of miR195, miR124a, miR372, miR521, and miR568; and/or
   e. the at least two miRNAs, or isoforms thereof, for determining saliva are selected from the group consisting of miR205, miR206, miR208, miR302c, miR509, miR510, miR515-5p, miR518c*, miR525, miR526b, miR551a, miR600, miR606, miR555, miR587, and miR658.

6. The method of claim 1, further comprising reverse transcribing the obtained RNA prior to the analyzing.

7. The method of claim 6, further comprising quantifying the obtained RNA.

* * * * *

SEQUENCE LISTING

```
<160> NUMBER OF SEQ ID NOS: 227

<210> SEQ ID NO 1
<211> LENGTH: 22
<212> TYPE: RNA
<213> ORGANISM: Homo sapiens

<400> SEQUENCE: 1
ugagguagua gguuguauag uu                                            22

<210> SEQ ID NO 2
<211> LENGTH: 22
<212> TYPE: RNA
<213> ORGANISM: Homo sapiens

<400> SEQUENCE: 2
ugagguagua gguugugugg uu                                            22

<210> SEQ ID NO 3
<211> LENGTH: 22
<212> TYPE: RNA
<213> ORGANISM: Homo sapiens

<400> SEQUENCE: 3
ugagguagua gguuguaugg uu                                            22

<210> SEQ ID NO 4
<211> LENGTH: 22
<212> TYPE: RNA
<213> ORGANISM: Homo sapiens

<400> SEQUENCE: 4
agagguagua gguugcauag uu                                            22

<210> SEQ ID NO 5
<211> LENGTH: 22
<212> TYPE: RNA
<213> ORGANISM: Homo sapiens
```

-continued

```
<400> SEQUENCE: 5
ugagguagga gguuguauag uu                                               22

<210> SEQ ID NO 6
<211> LENGTH: 22
<212> TYPE: RNA
<213> ORGANISM: Homo sapiens

<400> SEQUENCE: 6
ugagguagua gauuguauag uu                                               22

<210> SEQ ID NO 7
<211> LENGTH: 22
<212> TYPE: RNA
<213> ORGANISM: Homo sapiens

<400> SEQUENCE: 7
ugagguagua guuuguacag uu                                               22

<210> SEQ ID NO 8
<211> LENGTH: 22
<212> TYPE: RNA
<213> ORGANISM: Homo sapiens

<400> SEQUENCE: 8
ugagguagua guuugugcug uu                                               22

<210> SEQ ID NO 9
<211> LENGTH: 23
<212> TYPE: RNA
<213> ORGANISM: Homo sapiens

<400> SEQUENCE: 9
uggaagacua gugauuuugu ugu                                              23

<210> SEQ ID NO 10
<211> LENGTH: 22
<212> TYPE: RNA
<213> ORGANISM: Homo sapiens

<400> SEQUENCE: 10
uagcagcaca uaaugguuug ug                                               22

<210> SEQ ID NO 11
<211> LENGTH: 22
<212> TYPE: RNA
<213> ORGANISM: Homo sapiens

<400> SEQUENCE: 11
uagcagcaca ucaugguuua ca                                               22

<210> SEQ ID NO 12
<211> LENGTH: 22
<212> TYPE: RNA
<213> ORGANISM: Homo sapiens

<400> SEQUENCE: 12
uagcagcacg uaaauauugg cg                                               22

<210> SEQ ID NO 13
<211> LENGTH: 23
<212> TYPE: RNA
<213> ORGANISM: Homo sapiens
```

-continued

```
<400> SEQUENCE: 13
caaagugcuu acagugcagg uag                                              23

<210> SEQ ID NO 14
<211> LENGTH: 23
<212> TYPE: RNA
<213> ORGANISM: Homo sapiens

<400> SEQUENCE: 14
uaaggugcau cuagugcaga uag                                              23

<210> SEQ ID NO 15
<211> LENGTH: 23
<212> TYPE: RNA
<213> ORGANISM: Homo sapiens

<400> SEQUENCE: 15
uaaggugcau cuagugcagu uag                                              23

<210> SEQ ID NO 16
<211> LENGTH: 23
<212> TYPE: RNA
<213> ORGANISM: Homo sapiens

<400> SEQUENCE: 16
acugcccuaa gugcuccuuc ugg                                              23

<210> SEQ ID NO 17
<211> LENGTH: 23
<212> TYPE: RNA
<213> ORGANISM: Homo sapiens

<400> SEQUENCE: 17
ugugcaaauc uaugcaaaac uga                                              23

<210> SEQ ID NO 18
<211> LENGTH: 23
<212> TYPE: RNA
<213> ORGANISM: Homo sapiens

<400> SEQUENCE: 18
uaaagugcuu auagugcagg uag                                              23

<210> SEQ ID NO 19
<211> LENGTH: 22
<212> TYPE: RNA
<213> ORGANISM: Homo sapiens

<400> SEQUENCE: 19
cauugcacuu gucucggucu ga                                               22

<210> SEQ ID NO 20
<211> LENGTH: 21
<212> TYPE: RNA
<213> ORGANISM: Homo sapiens

<400> SEQUENCE: 20
uucaaguaau ucaggauagg u                                                21

<210> SEQ ID NO 21
<211> LENGTH: 22
<212> TYPE: RNA
```

```
<213> ORGANISM: Homo sapiens

<400> SEQUENCE: 21
uguaaacauc cuacacucag cu                                           22

<210> SEQ ID NO 22
<211> LENGTH: 22
<212> TYPE: RNA
<213> ORGANISM: Homo sapiens

<400> SEQUENCE: 22
uguaaacauc cucgacugga ag                                           22

<210> SEQ ID NO 23
<211> LENGTH: 22
<212> TYPE: RNA
<213> ORGANISM: Homo sapiens

<400> SEQUENCE: 23
uguaaacauc cuugacugga ag                                           22

<210> SEQ ID NO 24
<211> LENGTH: 23
<212> TYPE: RNA
<213> ORGANISM: Homo sapiens

<400> SEQUENCE: 24
caaagugcug uucgugcagg uag                                          23

<210> SEQ ID NO 25
<211> LENGTH: 23
<212> TYPE: RNA
<213> ORGANISM: Homo sapiens

<400> SEQUENCE: 25
uuuggcacua gcacauuuuu gcu                                          23

<210> SEQ ID NO 26
<211> LENGTH: 23
<212> TYPE: RNA
<213> ORGANISM: Homo sapiens

<400> SEQUENCE: 26
agcagcauug uacagggcua uga                                          23

<210> SEQ ID NO 27
<211> LENGTH: 23
<212> TYPE: RNA
<213> ORGANISM: Homo sapiens

<400> SEQUENCE: 27
aaaagugcuu acagugcagg uag                                          23

<210> SEQ ID NO 28
<211> LENGTH: 21
<212> TYPE: RNA
<213> ORGANISM: Homo sapiens

<400> SEQUENCE: 28
uaaagugcug acagugcaga u                                            21

<210> SEQ ID NO 29
<211> LENGTH: 23
```

```
<212> TYPE: RNA
<213> ORGANISM: Homo sapiens

<400> SEQUENCE: 29
agcagcauug uacagggcua uca                                        23

<210> SEQ ID NO 30
<211> LENGTH: 22
<212> TYPE: RNA
<213> ORGANISM: Homo sapiens

<400> SEQUENCE: 30
ucguaccgug aguaauaaug cg                                         22

<210> SEQ ID NO 31
<211> LENGTH: 21
<212> TYPE: RNA
<213> ORGANISM: Homo sapiens

<400> SEQUENCE: 31
cauuauuacu uuugguacgc g                                          21

<210> SEQ ID NO 32
<211> LENGTH: 21
<212> TYPE: RNA
<213> ORGANISM: Homo sapiens

<400> SEQUENCE: 32
ucacagugaa ccggucucuu u                                          21

<210> SEQ ID NO 33
<211> LENGTH: 22
<212> TYPE: RNA
<213> ORGANISM: Homo sapiens

<400> SEQUENCE: 33
cagugcaaug uuaaaagggc au                                         22

<210> SEQ ID NO 34
<211> LENGTH: 22
<212> TYPE: RNA
<213> ORGANISM: Homo sapiens

<400> SEQUENCE: 34
ucagugcacu acagaacuuu gu                                         22

<210> SEQ ID NO 35
<211> LENGTH: 22
<212> TYPE: RNA
<213> ORGANISM: Homo sapiens

<400> SEQUENCE: 35
ucagugcauc acagaacuuu gu                                         22

<210> SEQ ID NO 36
<211> LENGTH: 22
<212> TYPE: RNA
<213> ORGANISM: Homo sapiens

<400> SEQUENCE: 36
aaaguucuga gacacuccga cu                                         22

<210> SEQ ID NO 37
```

```
<211> LENGTH: 22
<212> TYPE: RNA
<213> ORGANISM: Homo sapiens

<400> SEQUENCE: 37
aaguucuguu auacacucag gc                                              22

<210> SEQ ID NO 38
<211> LENGTH: 22
<212> TYPE: RNA
<213> ORGANISM: Homo sapiens

<400> SEQUENCE: 38
ucucccaacc cuuguaccag ug                                              22

<210> SEQ ID NO 39
<211> LENGTH: 21
<212> TYPE: RNA
<213> ORGANISM: Homo sapiens

<400> SEQUENCE: 39
ucgaggagcu cacagucuag u                                               21

<210> SEQ ID NO 40
<211> LENGTH: 21
<212> TYPE: RNA
<213> ORGANISM: Homo sapiens

<400> SEQUENCE: 40
cuagacugaa gcuccuugag g                                               21

<210> SEQ ID NO 41
<211> LENGTH: 23
<212> TYPE: RNA
<213> ORGANISM: Homo sapiens

<400> SEQUENCE: 41
aacauucaac gcugucggug agu                                             23

<210> SEQ ID NO 42
<211> LENGTH: 22
<212> TYPE: RNA
<213> ORGANISM: Homo sapiens

<400> SEQUENCE: 42
aacauucaac cugucggguga gu                                             22

<210> SEQ ID NO 43
<211> LENGTH: 24
<212> TYPE: RNA
<213> ORGANISM: Homo sapiens

<400> SEQUENCE: 43
uuuggcaaug guagaacuca cacu                                            24

<210> SEQ ID NO 44
<211> LENGTH: 21
<212> TYPE: RNA
<213> ORGANISM: Homo sapiens

<400> SEQUENCE: 44
ugguucuaga cuugccaacu a                                               21
```

```
<210> SEQ ID NO 45
<211> LENGTH: 22
<212> TYPE: RNA
<213> ORGANISM: Homo sapiens

<400> SEQUENCE: 45
uauggcacug guagaauuca cu                                              22

<210> SEQ ID NO 46
<211> LENGTH: 22
<212> TYPE: RNA
<213> ORGANISM: Homo sapiens

<400> SEQUENCE: 46
uggagagaaa ggcaguuccu ga                                              22

<210> SEQ ID NO 47
<211> LENGTH: 22
<212> TYPE: RNA
<213> ORGANISM: Homo sapiens

<400> SEQUENCE: 47
ugauauguuu gauauauuag gu                                              22

<210> SEQ ID NO 48
<211> LENGTH: 23
<212> TYPE: RNA
<213> ORGANISM: Homo sapiens

<400> SEQUENCE: 48
caacggaauc ccaaaagcag cug                                             23

<210> SEQ ID NO 49
<211> LENGTH: 22
<212> TYPE: RNA
<213> ORGANISM: Homo sapiens

<400> SEQUENCE: 49
uguaacagca acuccaugug ga                                              22

<210> SEQ ID NO 50
<211> LENGTH: 21
<212> TYPE: RNA
<213> ORGANISM: Homo sapiens

<400> SEQUENCE: 50
uagcagcaca gaaauauugg c                                               21

<210> SEQ ID NO 51
<211> LENGTH: 22
<212> TYPE: RNA
<213> ORGANISM: Homo sapiens

<400> SEQUENCE: 51
cugugcgugu gacagcggcu ga                                              22

<210> SEQ ID NO 52
<211> LENGTH: 21
<212> TYPE: RNA
<213> ORGANISM: Homo sapiens

<400> SEQUENCE: 52
augaccuaug aauugacaga c                                               21
```

-continued

```
<210> SEQ ID NO 53
<211> LENGTH: 23
<212> TYPE: RNA
<213> ORGANISM: Homo sapiens

<400> SEQUENCE: 53
cagugcaaua guauugucaa agc                                              23

<210> SEQ ID NO 54
<211> LENGTH: 23
<212> TYPE: RNA
<213> ORGANISM: Homo sapiens

<400> SEQUENCE: 54
cagugcaaug auauugucaa agc                                              23

<210> SEQ ID NO 55
<211> LENGTH: 20
<212> TYPE: RNA
<213> ORGANISM: Homo sapiens

<400> SEQUENCE: 55
acugccccag gugcugcugg                                                  20

<210> SEQ ID NO 56
<211> LENGTH: 21
<212> TYPE: RNA
<213> ORGANISM: Homo sapiens

<400> SEQUENCE: 56
gccccugggc cuauccuaga a                                                21

<210> SEQ ID NO 57
<211> LENGTH: 22
<212> TYPE: RNA
<213> ORGANISM: Homo sapiens

<400> SEQUENCE: 57
cuagguaugg ucccagggau cc                                               22

<210> SEQ ID NO 58
<211> LENGTH: 23
<212> TYPE: RNA
<213> ORGANISM: Homo sapiens

<400> SEQUENCE: 58
ucccuguccu ccaggagcuc acg                                              23

<210> SEQ ID NO 59
<211> LENGTH: 23
<212> TYPE: RNA
<213> ORGANISM: Homo sapiens

<400> SEQUENCE: 59
ugagcgccuc gacgacagag ccg                                              23

<210> SEQ ID NO 60
<211> LENGTH: 22
<212> TYPE: RNA
<213> ORGANISM: Homo sapiens

<400> SEQUENCE: 60
uuauaaagca augagacuga uu                                               22
```

```
<210> SEQ ID NO 61
<211> LENGTH: 22
<212> TYPE: RNA
<213> ORGANISM: Homo sapiens

<400> SEQUENCE: 61 cgggug gauc acgaugcaau uu                                              22

<210> SEQ ID NO 62
<211> LENGTH: 22
<212> TYPE: RNA
<213> ORGANISM: Homo sapiens

<400> SEQUENCE: 62
uuauaauaca accugauaag ug                                               22

<210> SEQ ID NO 63
<211> LENGTH: 23
<212> TYPE: RNA
<213> ORGANISM: Homo sapiens

<400> SEQUENCE: 63
aaugacacga ucacucccgu uga                                              23

<210> SEQ ID NO 64
<211> LENGTH: 22
<212> TYPE: RNA
<213> ORGANISM: Homo sapiens

<400> SEQUENCE: 64
uccuguacug agcugccccg ag                                               22

<210> SEQ ID NO 65
<211> LENGTH: 21
<212> TYPE: RNA
<213> ORGANISM: Homo sapiens

<400> SEQUENCE: 65
cggggcagcu caguacagga u                                                21

<210> SEQ ID NO 66
<211> LENGTH: 23
<212> TYPE: RNA
<213> ORGANISM: Homo sapiens

<400> SEQUENCE: 66
uaauccuugc uaccugggug aga                                              23

<210> SEQ ID NO 67
<211> LENGTH: 22
<212> TYPE: RNA
<213> ORGANISM: Homo sapiens

<400> SEQUENCE: 67
ucagcaaaca uuuauugugu gc                                               22

<210> SEQ ID NO 68
<211> LENGTH: 22
<212> TYPE: RNA
<213> ORGANISM: Homo sapiens

<400> SEQUENCE: 68
```

```
aaaaguaauu gugguuuuug cc                                              22

<210> SEQ ID NO 69
<211> LENGTH: 22
<212> TYPE: RNA
<213> ORGANISM: Homo sapiens

<400> SEQUENCE: 69
caaaaaccac aguuucuuuu gc                                              22

<210> SEQ ID NO 70
<211> LENGTH: 22
<212> TYPE: RNA
<213> ORGANISM: Homo sapiens

<400> SEQUENCE: 70
auauuaccau uagcucaucu uu                                              22

<210> SEQ ID NO 71
<211> LENGTH: 22
<212> TYPE: RNA
<213> ORGANISM: Homo sapiens

<400> SEQUENCE: 71
gaugagcuca uuguaauaug ag                                              22

<210> SEQ ID NO 72
<211> LENGTH: 22
<212> TYPE: RNA
<213> ORGANISM: Homo sapiens

<400> SEQUENCE: 72
aagaugugga aaaauuggaa uc                                              22

<210> SEQ ID NO 73
<211> LENGTH: 22
<212> TYPE: RNA
<213> ORGANISM: Homo sapiens

<400> SEQUENCE: 73
auucuaauuu cuccacgucu uu                                              22

<210> SEQ ID NO 74
<211> LENGTH: 23
<212> TYPE: RNA
<213> ORGANISM: Homo sapiens

<400> SEQUENCE: 74 uucauuggu auaaccgcg auu                                               23

<210> SEQ ID NO 75
<211> LENGTH: 22
<212> TYPE: RNA
<213> ORGANISM: Homo sapiens

<400> SEQUENCE: 75
uugagaauga ugaaucauua gg                                              22

<210> SEQ ID NO 76
<211> LENGTH: 21
<212> TYPE: RNA
<213> ORGANISM: Homo sapiens

<400> SEQUENCE: 76
```

-continued

```
ucuuguguuc ucuagaucag u                                          21

<210> SEQ ID NO 77
<211> LENGTH: 22
<212> TYPE: RNA
<213> ORGANISM: Homo sapiens

<400> SEQUENCE: 77
gagcuuauuc auaaaagugc ag                                         22

<210> SEQ ID NO 78
<211> LENGTH: 21
<212> TYPE: RNA
<213> ORGANISM: Homo sapiens

<400> SEQUENCE: 78
uaauuuuaug uauaagcuag u                                          21

<210> SEQ ID NO 79
<211> LENGTH: 21
<212> TYPE: RNA
<213> ORGANISM: Homo sapiens

<400> SEQUENCE: 79
cacaagguau ugguauuacc u                                          21

<210> SEQ ID NO 80
<211> LENGTH: 22
<212> TYPE: RNA
<213> ORGANISM: Homo sapiens

<400> SEQUENCE: 80
gugagucucu aagaaaagag ga                                         22

<210> SEQ ID NO 81
<211> LENGTH: 22
<212> TYPE: RNA
<213> ORGANISM: Homo sapiens

<400> SEQUENCE: 81
uuuaggauaa gcuugacuuu ug                                         22

<210> SEQ ID NO 82
<211> LENGTH: 21
<212> TYPE: RNA
<213> ORGANISM: Homo sapiens

<400> SEQUENCE: 82
aauggcgcca cuaggguugu g                                          21

<210> SEQ ID NO 83
<211> LENGTH: 22
<212> TYPE: RNA
<213> ORGANISM: Homo sapiens

<400> SEQUENCE: 83
uacccauugc auaucggagu ug                                         22

<210> SEQ ID NO 84
<211> LENGTH: 22
<212> TYPE: RNA
<213> ORGANISM: Homo sapiens
```

```
<400> SEQUENCE: 84
aaucauacac gguugaccua uu                                          22

<210> SEQ ID NO 85
<211> LENGTH: 21
<212> TYPE: RNA
<213> ORGANISM: Homo sapiens

<400> SEQUENCE: 85
guucaaaucc agaucuauaa c                                           21

<210> SEQ ID NO 86
<211> LENGTH: 21
<212> TYPE: RNA
<213> ORGANISM: Homo sapiens

<400> SEQUENCE: 86
aucacauugc cagggauuuc c                                           21

<210> SEQ ID NO 87
<211> LENGTH: 21
<212> TYPE: RNA
<213> ORGANISM: Homo sapiens

<400> SEQUENCE: 87
aucacauugc cagggauuac c                                           21

<210> SEQ ID NO 88
<211> LENGTH: 21
<212> TYPE: RNA
<213> ORGANISM: Homo sapiens

<400> SEQUENCE: 88
uucacagugg cuaaguucug c                                           21

<210> SEQ ID NO 89
<211> LENGTH: 21
<212> TYPE: RNA
<213> ORGANISM: Homo sapiens

<400> SEQUENCE: 89
aggcaagaug cuggcauagc u                                           21

<210> SEQ ID NO 90
<211> LENGTH: 21
<212> TYPE: RNA
<213> ORGANISM: Homo sapiens

<400> SEQUENCE: 90
gugcauugua guugcauugc a                                           21

<210> SEQ ID NO 91
<211> LENGTH: 20
<212> TYPE: RNA
<213> ORGANISM: Homo sapiens

<400> SEQUENCE: 91
gugcauugcu guugcauugc                                             20

<210> SEQ ID NO 92
<211> LENGTH: 22
<212> TYPE: RNA
<213> ORGANISM: Homo sapiens
```

-continued

<400> SEQUENCE: 92 uucaacggguauuuauugagca                                                    22

<210> SEQ ID NO 93
<211> LENGTH: 22
<212> TYPE: RNA
<213> ORGANISM: Homo sapiens

<400> SEQUENCE: 93 acaggugagguucuugggagcc                                                    22

<210> SEQ ID NO 94
<211> LENGTH: 24
<212> TYPE: RNA
<213> ORGANISM: Homo sapiens

<400> SEQUENCE: 94 ucccugagacccuuuaaccuguga                                                  24

<210> SEQ ID NO 95
<211> LENGTH: 22
<212> TYPE: RNA
<213> ORGANISM: Homo sapiens

<400> SEQUENCE: 95 ucccugagacccuaacuuguga                                                    22

<210> SEQ ID NO 96
<211> LENGTH: 23
<212> TYPE: RNA
<213> ORGANISM: Homo sapiens

<400> SEQUENCE: 96 acuccauuuguuuugaugaugga                                                   23

<210> SEQ ID NO 97
<211> LENGTH: 22
<212> TYPE: RNA
<213> ORGANISM: Homo sapiens

<400> SEQUENCE: 97 uaacacugucugguaaagaugg                                                    22

<210> SEQ ID NO 98
<211> LENGTH: 21
<212> TYPE: RNA
<213> ORGANISM: Homo sapiens

<400> SEQUENCE: 98 ugagaugaagcacuguagcuc                                                     21

<210> SEQ ID NO 99
<211> LENGTH: 22
<212> TYPE: RNA
<213> ORGANISM: Homo sapiens

<400> SEQUENCE: 99 uagguuauccguguugccuucg                                                    22

<210> SEQ ID NO 100
<211> LENGTH: 23
<212> TYPE: RNA

```
<213> ORGANISM: Homo sapiens

<400> SEQUENCE: 100
aacauucauu gcugucggug ggu                                              23

<210> SEQ ID NO 101
<211> LENGTH: 22
<212> TYPE: RNA
<213> ORGANISM: Homo sapiens

<400> SEQUENCE: 101
ugccuacuga gcugauauca gu                                               22

<210> SEQ ID NO 102
<211> LENGTH: 22
<212> TYPE: RNA
<213> ORGANISM: Homo sapiens

<400> SEQUENCE: 102
aacuggcccu caaagucccg cu                                               22

<210> SEQ ID NO 103
<211> LENGTH: 22
<212> TYPE: RNA
<213> ORGANISM: Homo sapiens

<400> SEQUENCE: 103
acaguagucu gcacauuggu ua                                               22

<210> SEQ ID NO 104
<211> LENGTH: 23
<212> TYPE: RNA
<213> ORGANISM: Homo sapiens

<400> SEQUENCE: 104
cccaguguuc agacuaccug uuc                                              23

<210> SEQ ID NO 105
<211> LENGTH: 23
<212> TYPE: RNA
<213> ORGANISM: Homo sapiens

<400> SEQUENCE: 105
cccaguguuu agacuaucug uuc                                              23

<210> SEQ ID NO 106
<211> LENGTH: 22
<212> TYPE: RNA
<213> ORGANISM: Homo sapiens

<400> SEQUENCE: 106
uaauacugcc ugguaaugau ga                                               22

<210> SEQ ID NO 107
<211> LENGTH: 23
<212> TYPE: RNA
<213> ORGANISM: Homo sapiens

<400> SEQUENCE: 107
uaauacugcc ggguaaugau gga                                              23

<210> SEQ ID NO 108
<211> LENGTH: 22
```

<212> TYPE: RNA
<213> ORGANISM: Homo sapiens

<400> SEQUENCE: 108
gugaaauguu uaggaccacu ag                                          22

<210> SEQ ID NO 109
<211> LENGTH: 21
<212> TYPE: RNA
<213> ORGANISM: Homo sapiens

<400> SEQUENCE: 109
uugugcuuga ucuaaccaug u                                           21

<210> SEQ ID NO 110
<211> LENGTH: 22
<212> TYPE: RNA
<213> ORGANISM: Homo sapiens

<400> SEQUENCE: 110
ugucaguuug ucaaauaccc ca                                          22

<210> SEQ ID NO 111
<211> LENGTH: 22
<212> TYPE: RNA
<213> ORGANISM: Homo sapiens

<400> SEQUENCE: 111
cuccuauaug augccuuucu uc                                          22

<210> SEQ ID NO 112
<211> LENGTH: 21
<212> TYPE: RNA
<213> ORGANISM: Homo sapiens

<400> SEQUENCE: 112
gaacggcuuc auacaggagu u                                           21

<210> SEQ ID NO 113
<211> LENGTH: 22
<212> TYPE: RNA
<213> ORGANISM: Homo sapiens

<400> SEQUENCE: 113
aucacacaaa ggcaacuuuu gu                                          22

<210> SEQ ID NO 114
<211> LENGTH: 22
<212> TYPE: RNA
<213> ORGANISM: Homo sapiens

<400> SEQUENCE: 114
gaaguuguuc gugguggauu cg                                          22

<210> SEQ ID NO 115
<211> LENGTH: 23
<212> TYPE: RNA
<213> ORGANISM: Homo sapiens

<400> SEQUENCE: 115
acuucaccug guccacuagc cgu                                         23

<210> SEQ ID NO 116

```
<211> LENGTH: 23
<212> TYPE: RNA
<213> ORGANISM: Homo sapiens

<400> SEQUENCE: 116
agcucggucu gaggccccuc agu                                              23

<210> SEQ ID NO 117
<211> LENGTH: 23
<212> TYPE: RNA
<213> ORGANISM: Homo sapiens

<400> SEQUENCE: 117 ugagggcag agagcgagac uuu                                               23

<210> SEQ ID NO 118
<211> LENGTH: 23
<212> TYPE: RNA
<213> ORGANISM: Homo sapiens

<400> SEQUENCE: 118
uagugcaaua uugcuuauag ggu                                              23

<210> SEQ ID NO 119
<211> LENGTH: 22
<212> TYPE: RNA
<213> ORGANISM: Homo sapiens

<400> SEQUENCE: 119
aaaccguuac cauuacugag uu                                               22

<210> SEQ ID NO 120
<211> LENGTH: 22
<212> TYPE: RNA
<213> ORGANISM: Homo sapiens

<400> SEQUENCE: 120
ucaggcucag uccccucccg au                                               22

<210> SEQ ID NO 121
<211> LENGTH: 20
<212> TYPE: RNA
<213> ORGANISM: Homo sapiens

<400> SEQUENCE: 121 auccuagaa auuguucaua                                                   20

<210> SEQ ID NO 122
<211> LENGTH: 22
<212> TYPE: RNA
<213> ORGANISM: Homo sapiens

<400> SEQUENCE: 122
uaauacuguc ugguaaaacc gu                                               22

<210> SEQ ID NO 123
<211> LENGTH: 21
<212> TYPE: RNA
<213> ORGANISM: Homo sapiens

<400> SEQUENCE: 123
ugucuugcag gccgucaugc a                                                21
```

```
<210> SEQ ID NO 124
<211> LENGTH: 22
<212> TYPE: RNA
<213> ORGANISM: Homo sapiens

<400> SEQUENCE: 124
aacuguuugc agaggaaacu ga                                              22

<210> SEQ ID NO 125
<211> LENGTH: 22
<212> TYPE: RNA
<213> ORGANISM: Homo sapiens

<400> SEQUENCE: 125
cucaucugca aagaaguaag ug                                              22

<210> SEQ ID NO 126
<211> LENGTH: 22
<212> TYPE: RNA
<213> ORGANISM: Homo sapiens

<400> SEQUENCE: 126
ugaaacauac acgggaaacc uc                                              22

<210> SEQ ID NO 127
<211> LENGTH: 21
<212> TYPE: RNA
<213> ORGANISM: Homo sapiens

<400> SEQUENCE: 127
cagcagcaca cugugguuug u                                               21

<210> SEQ ID NO 128
<211> LENGTH: 22
<212> TYPE: RNA
<213> ORGANISM: Homo sapiens

<400> SEQUENCE: 128
ccucuagaug gaagcacugu cu                                              22

<210> SEQ ID NO 129
<211> LENGTH: 23
<212> TYPE: RNA
<213> ORGANISM: Homo sapiens

<400> SEQUENCE: 129
cuaauaguau cuaccacaau aaa                                             23

<210> SEQ ID NO 130
<211> LENGTH: 24
<212> TYPE: RNA
<213> ORGANISM: Homo sapiens

<400> SEQUENCE: 130 acuggggcu uucgggcucu gcgu                                             24

<210> SEQ ID NO 131
<211> LENGTH: 24
<212> TYPE: RNA
<213> ORGANISM: Homo sapiens

<400> SEQUENCE: 131
aaagacauag gauagaguca ccuc                                            24
```

```
<210> SEQ ID NO 132
<211> LENGTH: 19
<212> TYPE: RNA
<213> ORGANISM: Homo sapiens

<400> SEQUENCE: 132
aagugugcag ggcacuggu                                            19

<210> SEQ ID NO 133
<211> LENGTH: 22
<212> TYPE: RNA
<213> ORGANISM: Homo sapiens

<400> SEQUENCE: 133
uucccuuugu cauccuucgc cu                                        22

<210> SEQ ID NO 134
<211> LENGTH: 22
<212> TYPE: RNA
<213> ORGANISM: Homo sapiens

<400> SEQUENCE: 134
agaucgaccg uguuauauuc gc                                        22

<210> SEQ ID NO 135
<211> LENGTH: 21
<212> TYPE: RNA
<213> ORGANISM: Homo sapiens

<400> SEQUENCE: 135
aucauagagg aaaauccacg u                                         21

<210> SEQ ID NO 136
<211> LENGTH: 22
<212> TYPE: RNA
<213> ORGANISM: Homo sapiens

<400> SEQUENCE: 136
aucauagagg aaaauccaug uu                                        22

<210> SEQ ID NO 137
<211> LENGTH: 21
<212> TYPE: RNA
<213> ORGANISM: Homo sapiens

<400> SEQUENCE: 137
ugguagacua uggaacguag g                                         21

<210> SEQ ID NO 138
<211> LENGTH: 22
<212> TYPE: RNA
<213> ORGANISM: Homo sapiens

<400> SEQUENCE: 138
gugacaucac auauacggca gc                                        22

<210> SEQ ID NO 139
<211> LENGTH: 21
<212> TYPE: RNA
<213> ORGANISM: Homo sapiens

<400> SEQUENCE: 139
uuuugcaccu uuuggaguga a                                         21
```

```
<210> SEQ ID NO 140
<211> LENGTH: 23
<212> TYPE: RNA
<213> ORGANISM: Homo sapiens

<400> SEQUENCE: 140
uacccuguag aaccgaauuu gug                                              23

<210> SEQ ID NO 141
<211> LENGTH: 22
<212> TYPE: RNA
<213> ORGANISM: Homo sapiens

<400> SEQUENCE: 141
aacccguaga uccgaucuug ug                                               22

<210> SEQ ID NO 142
<211> LENGTH: 22
<212> TYPE: RNA
<213> ORGANISM: Homo sapiens

<400> SEQUENCE: 142
aacccguaga uccgaacuug ug                                               22

<210> SEQ ID NO 143
<211> LENGTH: 23
<212> TYPE: RNA
<213> ORGANISM: Homo sapiens

<400> SEQUENCE: 143
uauggcuuuu uauuccuaug uga                                              23

<210> SEQ ID NO 144
<211> LENGTH: 23
<212> TYPE: RNA
<213> ORGANISM: Homo sapiens

<400> SEQUENCE: 144
uauggcuuuu cauuccuaug uga                                              23

<210> SEQ ID NO 145
<211> LENGTH: 23
<212> TYPE: RNA
<213> ORGANISM: Homo sapiens

<400> SEQUENCE: 145
ucuggcuccg ugucuucacu ccc                                              23

<210> SEQ ID NO 146
<211> LENGTH: 22
<212> TYPE: RNA
<213> ORGANISM: Homo sapiens

<400> SEQUENCE: 146
uucccuuugu cauccuaugc cu                                               22

<210> SEQ ID NO 147
<211> LENGTH: 22
<212> TYPE: RNA
<213> ORGANISM: Homo sapiens

<400> SEQUENCE: 147
```
uggcagugua uuguuagcug gu                                                    22

<210> SEQ ID NO 148
<211> LENGTH: 22
<212> TYPE: RNA
<213> ORGANISM: Homo sapiens

<400> SEQUENCE: 148
aggcagugua uuguuagcug gc                                                    22

<210> SEQ ID NO 149
<211> LENGTH: 23
<212> TYPE: RNA
<213> ORGANISM: Homo sapiens

<400> SEQUENCE: 149
ugauuguagc cuuuuggagu aga                                                   23

<210> SEQ ID NO 150
<211> LENGTH: 23
<212> TYPE: RNA
<213> ORGANISM: Homo sapiens

<400> SEQUENCE: 150
uacuccagag ggcgucacuc aug                                                   23

<210> SEQ ID NO 151
<211> LENGTH: 18
<212> TYPE: RNA
<213> ORGANISM: Homo sapiens

<400> SEQUENCE: 151
uucacaggga ggugucau                                                         18

<210> SEQ ID NO 152
<211> LENGTH: 22
<212> TYPE: RNA
<213> ORGANISM: Homo sapiens

<400> SEQUENCE: 152
aucgugcauc ccuuuagagu gu                                                    22

<210> SEQ ID NO 153
<211> LENGTH: 22
<212> TYPE: RNA
<213> ORGANISM: Homo sapiens

<400> SEQUENCE: 153
cucuagaggg aagcacuuuc uc                                                    22

<210> SEQ ID NO 154
<211> LENGTH: 22
<212> TYPE: RNA
<213> ORGANISM: Homo sapiens

<400> SEQUENCE: 154
caaagugccu cccuuuagag ug                                                    22

<210> SEQ ID NO 155
<211> LENGTH: 22
<212> TYPE: RNA
<213> ORGANISM: Homo sapiens

<400> SEQUENCE: 155

```
aagugccucc uuuuagagug uu                                          22

<210> SEQ ID NO 156
<211> LENGTH: 22
<212> TYPE: RNA
<213> ORGANISM: Homo sapiens

<400> SEQUENCE: 156
aaagugcuuc ccuuuggacu gu                                          22

<210> SEQ ID NO 157
<211> LENGTH: 21
<212> TYPE: RNA
<213> ORGANISM: Homo sapiens

<400> SEQUENCE: 157
aaagugcuuc cuuuuugagg g                                           21

<210> SEQ ID NO 158
<211> LENGTH: 24
<212> TYPE: RNA
<213> ORGANISM: Homo sapiens

<400> SEQUENCE: 158
acaaagugcu ucccuuuaga gugu                                        24

<210> SEQ ID NO 159
<211> LENGTH: 22
<212> TYPE: RNA
<213> ORGANISM: Homo sapiens

<400> SEQUENCE: 159
acaaagugcu ucccuuuaga gu                                          22

<210> SEQ ID NO 160
<211> LENGTH: 22
<212> TYPE: RNA
<213> ORGANISM: Homo sapiens

<400> SEQUENCE: 160
uacugcagac guggcaauca ug                                          22

<210> SEQ ID NO 161
<211> LENGTH: 22
<212> TYPE: RNA
<213> ORGANISM: Homo sapiens

<400> SEQUENCE: 161
ugauugguac gucugugggu ag                                          22

<210> SEQ ID NO 162
<211> LENGTH: 21
<212> TYPE: RNA
<213> ORGANISM: Homo sapiens

<400> SEQUENCE: 162
auugacacuu cugugaguag a                                           21

<210> SEQ ID NO 163
<211> LENGTH: 18
<212> TYPE: RNA
<213> ORGANISM: Homo sapiens
```

```
<400> SEQUENCE: 163
ugcuuccuuu cagagggu                                              18

<210> SEQ ID NO 164
<211> LENGTH: 20
<212> TYPE: RNA
<213> ORGANISM: Homo sapiens

<400> SEQUENCE: 164
cugcaaaggg aagcccuuuc                                            20

<210> SEQ ID NO 165
<211> LENGTH: 22
<212> TYPE: RNA
<213> ORGANISM: Homo sapiens

<400> SEQUENCE: 165
gaaagcgcuu cccuuugcug ga                                         22

<210> SEQ ID NO 166
<211> LENGTH: 23
<212> TYPE: RNA
<213> ORGANISM: Homo sapiens

<400> SEQUENCE: 166
caaagcgcuu cucuuuagag ugu                                        23

<210> SEQ ID NO 167
<211> LENGTH: 21
<212> TYPE: RNA
<213> ORGANISM: Homo sapiens

<400> SEQUENCE: 167
aaagcgcuuc ccuucagagu g                                          21

<210> SEQ ID NO 168
<211> LENGTH: 22
<212> TYPE: RNA
<213> ORGANISM: Homo sapiens

<400> SEQUENCE: 168
uucuccaaaa gggagcacuu uc                                         22

<210> SEQ ID NO 169
<211> LENGTH: 20
<212> TYPE: RNA
<213> ORGANISM: Homo sapiens

<400> SEQUENCE: 169
cuacaaaggg aagcccuuuc                                            20

<210> SEQ ID NO 170
<211> LENGTH: 22
<212> TYPE: RNA
<213> ORGANISM: Homo sapiens

<400> SEQUENCE: 170
aaagugcuuc ucuuuggugg gu                                         22

<210> SEQ ID NO 171
<211> LENGTH: 21
<212> TYPE: RNA
<213> ORGANISM: Homo sapiens
```

<400> SEQUENCE: 171
gaaggcgcuu cccuuuggag u                                            21

<210> SEQ ID NO 172
<211> LENGTH: 22
<212> TYPE: RNA
<213> ORGANISM: Homo sapiens

<400> SEQUENCE: 172
cuacaaaggg aagcacuuuc uc                                           22

<210> SEQ ID NO 173
<211> LENGTH: 22
<212> TYPE: RNA
<213> ORGANISM: Homo sapiens

<400> SEQUENCE: 173
cucuagaggg aagcacuuuc ug                                           22

<210> SEQ ID NO 174
<211> LENGTH: 21
<212> TYPE: RNA
<213> ORGANISM: Homo sapiens

<400> SEQUENCE: 174
ugacaacuau ggaugagcuc u                                            21

<210> SEQ ID NO 175
<211> LENGTH: 21
<212> TYPE: RNA
<213> ORGANISM: Homo sapiens

<400> SEQUENCE: 175
cuucuugugc ucuaggauug u                                            21

<210> SEQ ID NO 176
<211> LENGTH: 23
<212> TYPE: RNA
<213> ORGANISM: Homo sapiens

<400> SEQUENCE: 176
gcgaggaccc cucgggucu gac                                           23

<210> SEQ ID NO 177
<211> LENGTH: 22
<212> TYPE: RNA
<213> ORGANISM: Homo sapiens

<400> SEQUENCE: 177
uggcaguguc uuagcugguu gu                                           22

<210> SEQ ID NO 178
<211> LENGTH: 20
<212> TYPE: RNA
<213> ORGANISM: Homo sapiens

<400> SEQUENCE: 178
uaaggcacgc ggugaaugcc                                              20

<210> SEQ ID NO 179
<211> LENGTH: 23
<212> TYPE: RNA

```
<213> ORGANISM: Homo sapiens

<400> SEQUENCE: 179
aaagugcugc gacauuugag cgu                                             23

<210> SEQ ID NO 180
<211> LENGTH: 22
<212> TYPE: RNA
<213> ORGANISM: Homo sapiens

<400> SEQUENCE: 180
aaugcaccug ggcaaggauu ca                                              22

<210> SEQ ID NO 181
<211> LENGTH: 21
<212> TYPE: RNA
<213> ORGANISM: Homo sapiens

<400> SEQUENCE: 181
auccuugcua ucugggugcu a                                               21

<210> SEQ ID NO 182
<211> LENGTH: 22
<212> TYPE: RNA
<213> ORGANISM: Homo sapiens

<400> SEQUENCE: 182
aacgcacuuc ccuuuagagu gu                                              22

<210> SEQ ID NO 183
<211> LENGTH: 20
<212> TYPE: RNA
<213> ORGANISM: Homo sapiens

<400> SEQUENCE: 183
auguauaaau guauacacac                                                 20

<210> SEQ ID NO 184
<211> LENGTH: 19
<212> TYPE: RNA
<213> ORGANISM: Homo sapiens

<400> SEQUENCE: 184
gagccaguug gacaggagc                                                  19

<210> SEQ ID NO 185
<211> LENGTH: 23
<212> TYPE: RNA
<213> ORGANISM: Homo sapiens

<400> SEQUENCE: 185
uacccuguag auccgaauuu gug                                             23

<210> SEQ ID NO 186
<211> LENGTH: 23
<212> TYPE: RNA
<213> ORGANISM: Homo sapiens

<400> SEQUENCE: 186
uuauugcuua agaauacgcg uag                                             23

<210> SEQ ID NO 187
<211> LENGTH: 22
```

```
<212> TYPE: RNA
<213> ORGANISM: Homo sapiens

<400> SEQUENCE: 187
uccuucauuc caccggaguc ug                                              22

<210> SEQ ID NO 188
<211> LENGTH: 22
<212> TYPE: RNA
<213> ORGANISM: Homo sapiens

<400> SEQUENCE: 188
uggaauguaa ggaagugugu gg                                              22

<210> SEQ ID NO 189
<211> LENGTH: 22
<212> TYPE: RNA
<213> ORGANISM: Homo sapiens

<400> SEQUENCE: 189
auaagacgag caaaaagcuu gu                                              22

<210> SEQ ID NO 190
<211> LENGTH: 22
<212> TYPE: RNA
<213> ORGANISM: Homo sapiens

<400> SEQUENCE: 190
auaagacgaa caaaagguuu gu                                              22

<210> SEQ ID NO 191
<211> LENGTH: 22
<212> TYPE: RNA
<213> ORGANISM: Homo sapiens

<400> SEQUENCE: 191
aaaucucugc aggcaaaugu ga                                              22

<210> SEQ ID NO 192
<211> LENGTH: 22
<212> TYPE: RNA
<213> ORGANISM: Homo sapiens

<400> SEQUENCE: 192
uaaucucagc uggcaacugu ga                                              22

<210> SEQ ID NO 193
<211> LENGTH: 23
<212> TYPE: RNA
<213> ORGANISM: Homo sapiens

<400> SEQUENCE: 193
uaagugcuuc cauguuuugg uga                                             23

<210> SEQ ID NO 194
<211> LENGTH: 22
<212> TYPE: RNA
<213> ORGANISM: Homo sapiens

<400> SEQUENCE: 194
acuuuaacau ggaagugcuu uc                                              22

<210> SEQ ID NO 195
```

```
<211> LENGTH: 23
<212> TYPE: RNA
<213> ORGANISM: Homo sapiens

<400> SEQUENCE: 195
uaagugcuuc cauguuucag ugg                                              23

<210> SEQ ID NO 196
<211> LENGTH: 22
<212> TYPE: RNA
<213> ORGANISM: Homo sapiens

<400> SEQUENCE: 196
uuuaacaugg ggguaccugc ug                                               22

<210> SEQ ID NO 197
<211> LENGTH: 23
<212> TYPE: RNA
<213> ORGANISM: Homo sapiens

<400> SEQUENCE: 197
ugucugcccg caugccugcc ucu                                              23

<210> SEQ ID NO 198
<211> LENGTH: 22
<212> TYPE: RNA
<213> ORGANISM: Homo sapiens

<400> SEQUENCE: 198
agaucagaag gugauugugg cu                                               22

<210> SEQ ID NO 199
<211> LENGTH: 23
<212> TYPE: RNA
<213> ORGANISM: Homo sapiens

<400> SEQUENCE: 199
uuucaagcca gggggcguuu uuc                                              23

<210> SEQ ID NO 200
<211> LENGTH: 21
<212> TYPE: RNA
<213> ORGANISM: Homo sapiens

<400> SEQUENCE: 200
uuaagacuug cagugauguu u                                                21

<210> SEQ ID NO 201
<211> LENGTH: 22
<212> TYPE: RNA
<213> ORGANISM: Homo sapiens

<400> SEQUENCE: 201
aacaucacag caagucugug cu                                               22

<210> SEQ ID NO 202
<211> LENGTH: 22
<212> TYPE: RNA
<213> ORGANISM: Homo sapiens

<400> SEQUENCE: 202
ugauugguac gucugugggu ag                                               22
```

```
<210> SEQ ID NO 203
<211> LENGTH: 22
<212> TYPE: RNA
<213> ORGANISM: Homo sapiens

<400> SEQUENCE: 203
uacucaggag aguggcaauc ac                                              22

<210> SEQ ID NO 204
<211> LENGTH: 24
<212> TYPE: RNA
<213> ORGANISM: Homo sapiens

<400> SEQUENCE: 204
uucuccaaaa gaaagcacuu ucug                                            24

<210> SEQ ID NO 205
<211> LENGTH: 23
<212> TYPE: RNA
<213> ORGANISM: Homo sapiens

<400> SEQUENCE: 205
ucucuggagg gaagcacuuu cug                                             23

<210> SEQ ID NO 206
<211> LENGTH: 22
<212> TYPE: RNA
<213> ORGANISM: Homo sapiens

<400> SEQUENCE: 206
aaagugcauc cuuuuagagg uu                                              22

<210> SEQ ID NO 207
<211> LENGTH: 22
<212> TYPE: RNA
<213> ORGANISM: Homo sapiens

<400> SEQUENCE: 207
cucuagaggg aagcgcuuuc ug                                              22

<210> SEQ ID NO 208
<211> LENGTH: 21
<212> TYPE: RNA
<213> ORGANISM: Homo sapiens

<400> SEQUENCE: 208
cuccagaggg augcacuuuc u                                               21

<210> SEQ ID NO 209
<211> LENGTH: 22
<212> TYPE: RNA
<213> ORGANISM: Homo sapiens

<400> SEQUENCE: 209
gaaggcgcuu cccuuuagag cg                                              22

<210> SEQ ID NO 210
<211> LENGTH: 23
<212> TYPE: RNA
<213> ORGANISM: Homo sapiens

<400> SEQUENCE: 210
cucuugaggg aagcacuuuc ugu                                             23
```

```
<210> SEQ ID NO 211
<211> LENGTH: 22
<212> TYPE: RNA
<213> ORGANISM: Homo sapiens

<400> SEQUENCE: 211
caagaaccuc aguugcuuuu gu                                           22

<210> SEQ ID NO 212
<211> LENGTH: 22
<212> TYPE: RNA
<213> ORGANISM: Homo sapiens

<400> SEQUENCE: 212
aaaaguaauu gugguuuugg cc                                           22

<210> SEQ ID NO 213
<211> LENGTH: 21
<212> TYPE: RNA
<213> ORGANISM: Homo sapiens

<400> SEQUENCE: 213
gcgacccacu cuugguuucc a                                            21

<210> SEQ ID NO 214
<211> LENGTH: 21
<212> TYPE: RNA
<213> ORGANISM: Homo sapiens

<400> SEQUENCE: 214
aaaacgguga gauuuuguuu u                                            21

<210> SEQ ID NO 215
<211> LENGTH: 21
<212> TYPE: RNA
<213> ORGANISM: Homo sapiens

<400> SEQUENCE: 215
uagauaaaau auugguaccu g                                            21

<210> SEQ ID NO 216
<211> LENGTH: 23
<212> TYPE: RNA
<213> ORGANISM: Homo sapiens

<400> SEQUENCE: 216
acuuacagac aagagccuug cuc                                          23

<210> SEQ ID NO 217
<211> LENGTH: 19
<212> TYPE: RNA
<213> ORGANISM: Homo sapiens

<400> SEQUENCE: 217
aggcugcgga auucaggac                                               19

<210> SEQ ID NO 218
<211> LENGTH: 21
<212> TYPE: RNA
<213> ORGANISM: Homo sapiens

<400> SEQUENCE: 218
aaacuacuga aaaucaaaga u                                            21
```

```
<210> SEQ ID NO 219
<211> LENGTH: 22
<212> TYPE: RNA
<213> ORGANISM: Homo sapiens

<400> SEQUENCE: 219
acuuguaugc uagcucaggu ag                                              22

<210> SEQ ID NO 220
<211> LENGTH: 21
<212> TYPE: RNA
<213> ORGANISM: Homo sapiens

<400> SEQUENCE: 220
guggcugcac ucacuuccuu c                                               21

<210> SEQ ID NO 221
<211> LENGTH: 25
<212> TYPE: RNA
<213> ORGANISM: Homo sapiens

<400> SEQUENCE: 221
ggcggaggga aguagguccg uuggu                                           25

<210> SEQ ID NO 222
<211> LENGTH: 23
<212> TYPE: RNA
<213> ORGANISM: Homo sapiens

<400> SEQUENCE: 222
caguaacaaa gauucauccu ugu                                             23

<210> SEQ ID NO 223
<211> LENGTH: 23
<212> TYPE: RNA
<213> ORGANISM: Homo sapiens

<400> SEQUENCE: 223
uucucgagga aagaagcacu uuc                                             23

<210> SEQ ID NO 224
<211> LENGTH: 21
<212> TYPE: RNA
<213> ORGANISM: Homo sapiens

<400> SEQUENCE: 224
aggguaagcu gaaccucuga u                                               21

<210> SEQ ID NO 225
<211> LENGTH: 19
<212> TYPE: RNA
<213> ORGANISM: Homo sapiens

<400> SEQUENCE: 225
ugagcugcug uaccaaaau                                                  19

<210> SEQ ID NO 226
<211> LENGTH: 21
<212> TYPE: RNA
<213> ORGANISM: Homo sapiens

<400> SEQUENCE: 226
```

```
aguuaaugaa uccuggaaag u                                      21

<210> SEQ ID NO 227
<211> LENGTH: 21
<212> TYPE: RNA
<213> ORGANISM: Homo sapiens

<400> SEQUENCE: 227
uuuccauagg ugaugaguca c                                      21
```